(12) United States Patent
Matsumoto et al.

(10) Patent No.: US 8,436,990 B2
(45) Date of Patent: May 7, 2013

(54) MICROCHIP AND ANALYZING APPARATUS

(75) Inventors: Daisuke Matsumoto, Kyoto (JP);
Yasunori Shiraki, Kyoto (JP); Michio Naka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 216 days.

(21) Appl. No.: 13/055,240

(22) PCT Filed: Jul. 22, 2009

(86) PCT No.: PCT/JP2009/063129
§ 371 (c)(1),
(2), (4) Date: Jan. 21, 2011

(87) PCT Pub. No.: WO2010/010904
PCT Pub. Date: Jan. 28, 2010

(65) Prior Publication Data
US 2011/0134420 A1    Jun. 9, 2011

(30) Foreign Application Priority Data

Jul. 22, 2008    (JP) ................................. 2008-188846

(51) Int. Cl.
*G01N 21/05* (2006.01)
(52) U.S. Cl.
USPC .......................................... 356/246; 356/244
(58) Field of Classification Search .................. 356/244, 356/246, 417, 440, 432, 437; 436/525, 154, 436/524, 501; 422/82.05, 82.09, 82.11; 435/962
See application file for complete search history.

(56) References Cited

U.S. PATENT DOCUMENTS

| 4,110,043 | A | * | 8/1978 | Eisert ............................... 377/11 |
| 4,511,798 | A | | 4/1985 | Killingsworth ............... 250/231 |
| 4,907,884 | A | * | 3/1990 | Philips et al. ................. 356/336 |
| 5,030,843 | A | * | 7/1991 | Wakamura .................... 250/574 |
| 5,389,196 | A | * | 2/1995 | Bloomstein et al. ........... 216/66 |
| 5,750,410 | A | * | 5/1998 | Dou et al. ..................... 436/525 |
| 5,858,195 | A | | 1/1999 | Ramsey |
| 6,475,363 | B1 | | 11/2002 | Ramsey |

(Continued)

FOREIGN PATENT DOCUMENTS
CN    1168720 A    12/1997
CN    1567559 A    1/2005

(Continued)

OTHER PUBLICATIONS

International Search Report for PCT/JP2009/063129 (mailed Oct. 6, 2009).

*Primary Examiner* — Sang Nguyen
(74) *Attorney, Agent, or Firm* — Morgan, Lewis & Bockius LLP

(57) ABSTRACT

The present invention relates to a microchip 1 having a translucent member 11, a flow channel 10 or a cell formed at a side of the translucent member 11 where light enters, and an aperture 16 formed at a position corresponding to the flow channel 10 or the cell at a side of a translucent member 10 where light goes out. The aperture 16 has a light go-through surface 17 which causes light flux being emitted from the flow channel 10 or the cell to go through and a light reflective surface 18 that totally reflects the incident light flux. A width size W1 of the light go-through surface 17 is smaller than a width size W2 of the flow channel 10 or the cell.

21 Claims, 17 Drawing Sheets

U.S. PATENT DOCUMENTS

| | | | |
|---|---|---|---|
| 7,201,873 B2 | 4/2007 | Tanaka et al. | 422/58 |
| 7,443,502 B2 * | 10/2008 | Nozawa et al. | 356/244 |
| 8,303,908 B2 | 11/2012 | Taguchi et al. | |
| 2003/0232403 A1 | 12/2003 | Kellogg et al. | |
| 2004/0069639 A1 * | 4/2004 | Ono | 204/603 |
| 2005/0140971 A1 * | 6/2005 | Yamaguchi et al. | 356/246 |
| 2005/0175273 A1 * | 8/2005 | Iida et al. | 385/15 |
| 2006/0008381 A1 | 1/2006 | Taguchi et al. | 422/57 |
| 2007/0215817 A1 * | 9/2007 | Shirai et al. | 250/458.1 |
| 2009/0325315 A1 * | 12/2009 | Hirai et al. | 436/501 |

FOREIGN PATENT DOCUMENTS

| | | |
|---|---|---|
| CN | 1705884 A | 12/2005 |
| JP | 2000-297157 | 10/2000 |
| JP | 2000-321198 | 11/2000 |
| JP | 3877564 | 4/2003 |
| JP | 2003-130883 | 5/2003 |
| JP | 2003-279471 | 10/2003 |
| JP | 2004-077305 | 3/2004 |
| JP | 2004-138411 | 5/2004 |
| JP | 2004-150804 | 5/2004 |
| JP | 2007-298474 | 11/2007 |
| WO | 96/04547 A1 | 2/1996 |

* cited by examiner $D=D1>D2, C<V$

MICROCHIP AND ANALYZING APPARATUS

RELATED APPLICATIONS

The present application is a 371 filing based on PCT/JP2009/063129, filed Jul. 22, 2009, which claims priority to Japanese Application No. 2008-188846, filed Jul. 22, 2008, all of which are here by incorporated by reference in their entireties.

TECHNICAL FIELD

The present invention relates to a microchip having a flow channel or a cell irradiated with light for analyzing a sample, and an analyzing apparatus which uses the microchip.

BACKGROUND ART

As a method of analyzing samples, such as bloods, proteins and medicines, a technology using a microchip is well-known. Microchips have a minute flow channel, and a sample is caused to travel the minute flow channel by electrophoresis or capillary force, for example. When such a microchip is used, a cell provided in the minute flow channel or the halfway thereof is irradiated with light and the light through the minute flow channel or the cell is detected to analyze the sample. As optical analysis, absorptiometric method, fluorometry, etc., are known.

In order to improve the measurement accuracy of the optical analyzing method, it is necessary to eliminate internal stray light which is caused by aberration of lenses that configure an optical system and irregular reflection (excessive light which does not contribute to the measurement). For this reason, in the analyzing apparatus, unnecessary light is blocked by disposing an aperture on an optical axis.

As a method of blocking unnecessary light, for analytical tools like microchips, it has been proposed to form a tapered surface on a transparent member which configures a measurement cell. The tapered surface is for causing emitted light to scatter or reflect, and for allowing only light flux which has passed through the cell to reach a light receiving member.

However, according to the method of forming the tapered surface to block unnecessary light, it is difficult to cope with further advancement of refinement in μ-TAS (Micro Total Analysis System). That is, according to the structure that detaches/attaches the microchip to a specific observation point in the analyzing apparatus, positioning of the microchip to a precise location is restricted.

For example, when the microchip is detached/attached to the concave portion of a tray provided in the analyzing apparatus, it is necessary that the aperture size of the concave portion has some margin in consideration of a dimensional error of the microchip. Therefore, the precision of positioning the microchip can be ensured to some level, but because the microchip is not precisely set at a specific location, when the flow channel is made minute, it is difficult to make the observation point of the microchip and the optical axis precisely aligned with each other.

In order to make such alignment precise, for example, the dimensional precision of the microchip and that of the tray may be made strict and engagement of the microchip with the tray may be made strict, but in this case, the production cost increases. Moreover, a structure for an alignment using a positioning mechanism may be possible, but the apparatus becomes complex and expensive.

Patent Literature 1: U.S. Pat. No. 4,511,798
Patent Literature 2: Unexamined Japanese Patent Application KOKAI Publication No. 2007-298474

DISCLOSURE OF INVENTION

Problem to be Solved by the Invention

It is an object of the present invention to ensure an analytical precision of a sample with a simple structure while accepting a varying of the position of a microchip.

Means for Solving the Problem

A first aspect of the present invention provides a microchip having a translucent member, a flow channel or a cell formed at a side of the translucent member where light enters and an aperture formed in a position corresponding to the flow channel or the cell at a side of the translucent member where the light goes out. The aperture has a light go-through surface that causes light flux being emitted from the flow channel or the cell to go out, and a light reflective surface that causes incident light flux to be totally reflected. The width size of the light go-through surface is set to be smaller than the width size of the flow channel or the cell.

The light reflective surface includes, for example, a pair of inclined surfaces facing with each other. The pair of inclined surfaces is formed so that a distance between the pair of inclined surfaces becomes large as becoming apart from the light go-through surface. The light reflective surface may include a conical inclined surface. The conical inclined surface is formed so that a space of the conic becomes large as becoming apart from the light go-through surface.

The microchip of the present invention may further include a shading member preventing light from being emitted from portions other than the aperture.

The shading member is provided adjacent to the aperture for example. The shading member may be formed at a side face of the translucent member.

The translucent member may have a guide surface that guides light flux which does not pass through the light go-through surface to an exterior of the translucent member. In this case, it is desirable that the shading member is one which absorbs the light flux guided by the guide surface to the exterior of the translucent member.

The guide surface may be formed by making the side face of the translucent member inclined.

The microchip of the present invention may further include a second flow channel or a cell formed at the side of the translucent member where light enters and a second aperture formed in a position corresponding to the second flow channel or the cell at the light go-through surface side of the translucent member. In this case, it is desirable to provide the guide surface between the aperture and the second aperture. The guide surface may be an inner surface of a groove with a V-shaped cross section formed at the side of the translucent member where light goes out.

The microchip of the present invention may further include a cover that covers the flow channel or the cell at the side of the translucent member where light enters. In this case, it is desirable that the cover should have a concave portion for arranging an end of irradiating means that irradiates the flow channel or the cell with light.

Where the light source is an optical fiber, it is desirable that the concave portion should have a bottom face where a light go-through end surface of the optical fiber abuts or an end of the optical fiber including the light go-through end surface engages.

Preferably, the bottom face of the flow channel or the cell and the light go-through surface of the aperture are arranged on a same or substantially same axis.

When the flow channel or the cell is irradiated with light by the irradiating means, a light-entering surface relative to the flow channel or the cell is formed at a position satisfying a relationship C<V. C is the size of the light go-through surface of the irradiating means. V is a distance of a portion where a straight line interconnecting the edge of a light irradiating surface of the flow channel or the cell and the edge of the light go-through surface of the aperture intersects with an end surface of the irradiating means.

The microchip of the present invention is formed by, for example, pasting a second translucent member on the translucent member. The translucent member and the second translucent member have the aperture and a groove defining the flow channel. It is desirable that the aperture and the groove should be arranged at axisymmetric positions or at point-symmetrical positions in a planer view.

The translucent member and the second translucent member each may have a concave portion for positioning. It is desirable that the concave portions should be arranged at axisymmetric positions or at point-symmetrical positions in a planer view.

A second aspect of the present invention provided an analyzing apparatus which uses the microchip according to the first aspect of the present invention, and which includes a light source and an optical system. The light source and the optical system are arranged so as to cause light flux to enter into the flow channel or the cell, and to go out from the aperture. The optical system can irradiate the flow channel or the cell with light flux spreading in the direction of the short axis of the light go-through surface of the aperture.

The optical system can irradiate the flow channel or the cell with light flux having a long axis in the direction of the short axis of the light go-through surface of the aperture.

A third aspect of the present invention provides an analyzing apparatus that uses a microchip which has a cover covering the flow channel or the cell at the side of the translucent member where light enters and further including a concave portion, and the analyzing apparatus further includes irradiating means which irradiates the flow channel or the cell with light.

The irradiating means is provided so that a light go-through end abuts or engages with the concave portion of the cover of the microchip. It is desirable to fowl a second concave portion at the bottom face of the concave portion.

The irradiating means includes, for example, an optical fiber.

BEST MODE FOR CARRYING OUT THE INVENTION

Figure 1:
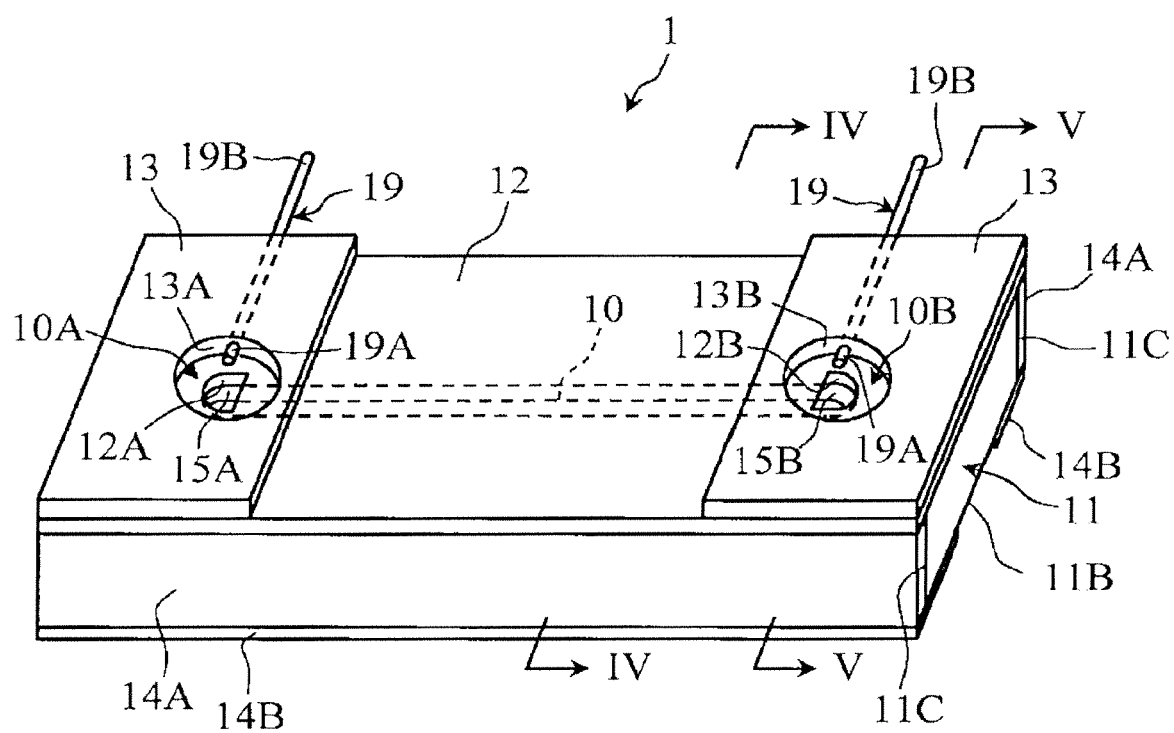
FIG. 1 is a whole perspective view showing an illustrative microchip according to the present invention.
Figure 2:
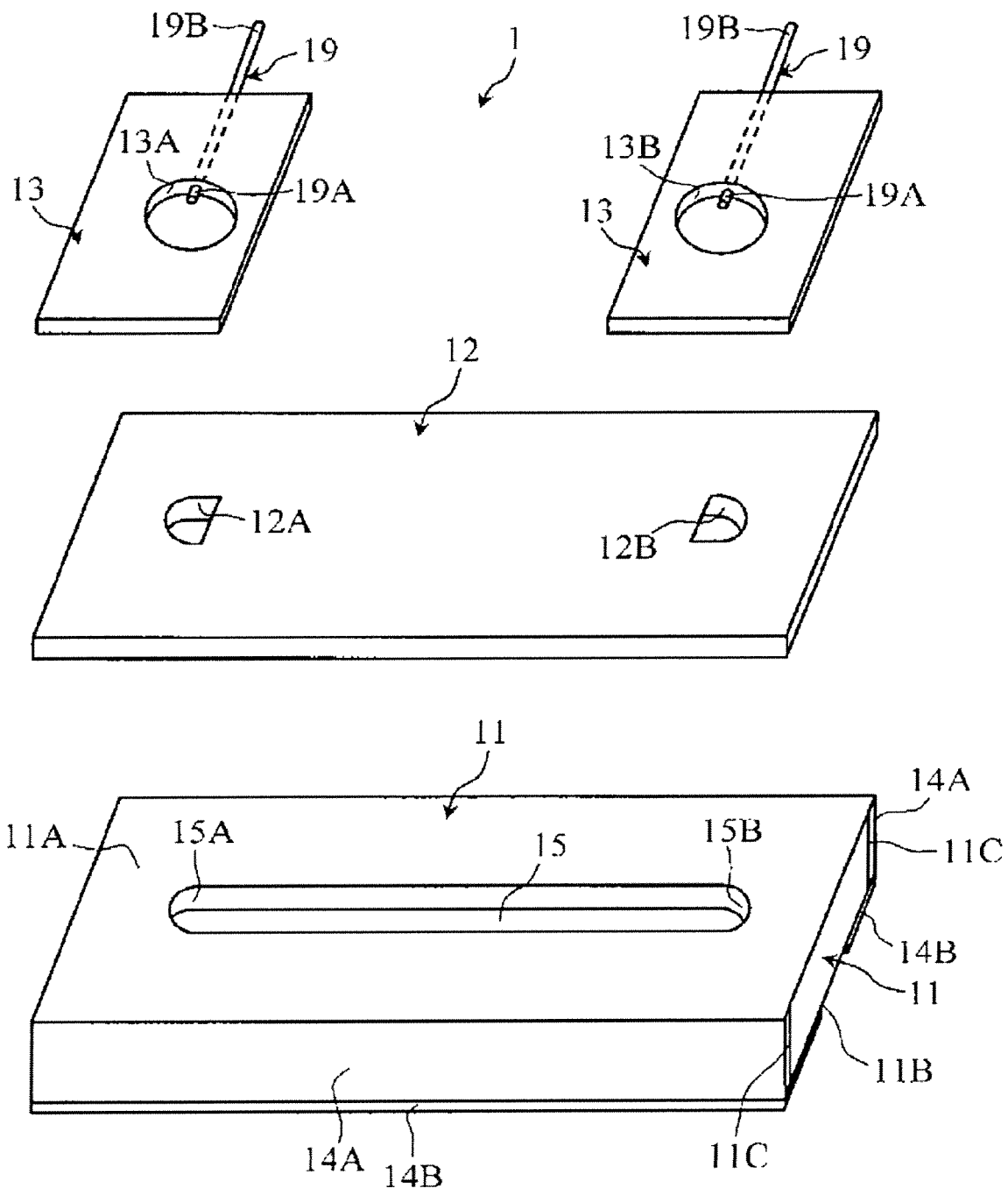
FIG. 2 is an exploded perspective view of the microchip shown in FIG. 1.

An embodiment of the present invention will be explained in detail with reference to the accompanying drawings.

First, a first embodiment of the present invention will be described with reference to FIG. 1 to FIG. 7.

As shown in FIG. 1 to FIG. 5, a microchip 1 is attached to and used for an analyzing apparatus 2 (see FIG. 5 and FIG. 6) to analyze samples, such as bloods, proteins and medicines. The microchip 1 is provided with a minute flow channel 10, and has a substrate 11, a cover 12, a tabular member 13, and shading members 14A, 14B.

The substrate 11 has a groove 15 and an aperture 16, and is formed by a transparent material. Examples of such a material for fowling the substrate 11 are PDMS, PMMA, PS and PC.

The groove 15 forms the flow channel 10 together with the cover 12. The groove 15 is formed so as to extend in the lengthwise direction of the substrate 11 in a top face 11A of the substrate 11.

Figure 3A:
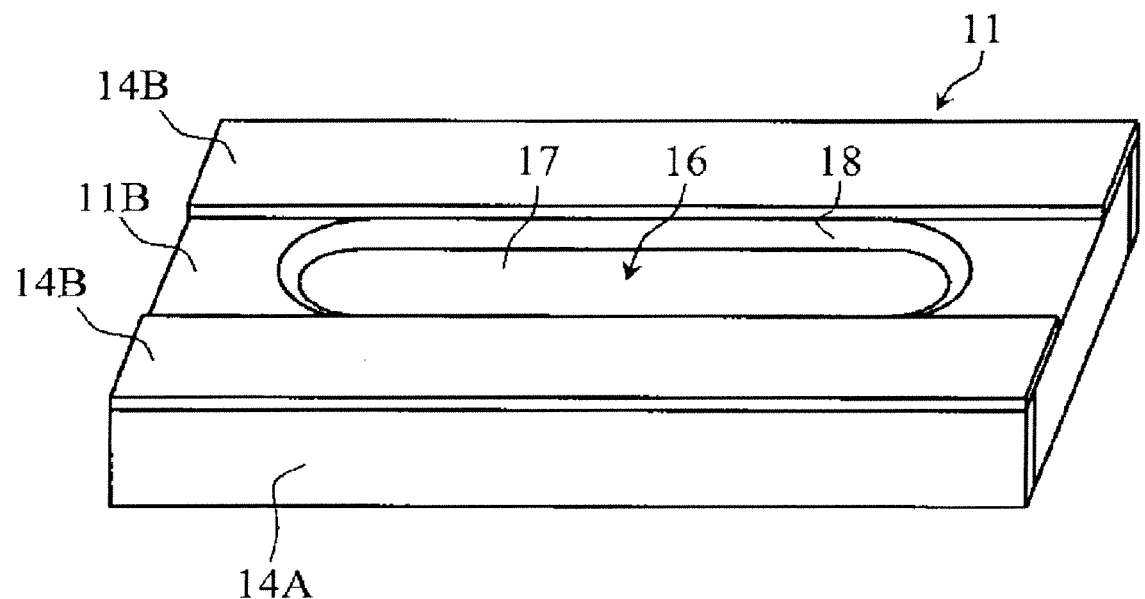
FIG. 3A and FIG. 3B are perspective views of a substrate in the microchip shown in FIG. 1 as viewed from the back.
Figure 3B:
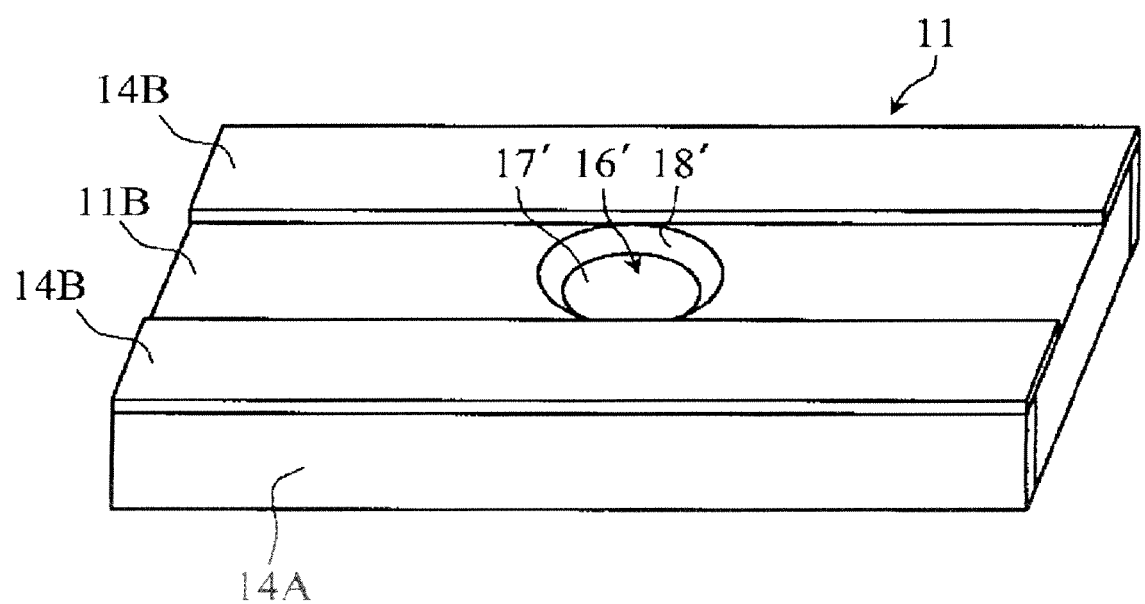

The aperture 16 functions as a diaphragm to eliminate internal stray light (excessive light which does not contribute to the measurement). As shown in FIG. 3A, the aperture 16 has a light go-through surface 17 and a pair of light reflective surfaces 18, and is formed in a lower face 11B of the substrate 11 so as to extend in the lengthwise direction of the substrate 11. As shown in FIG. 3B, an aperture 16' may be formed in the lower face 11B of the substrate 11 so as to have a light go-through surface 17' and a conical light reflective surface 18'.

Figure 4:
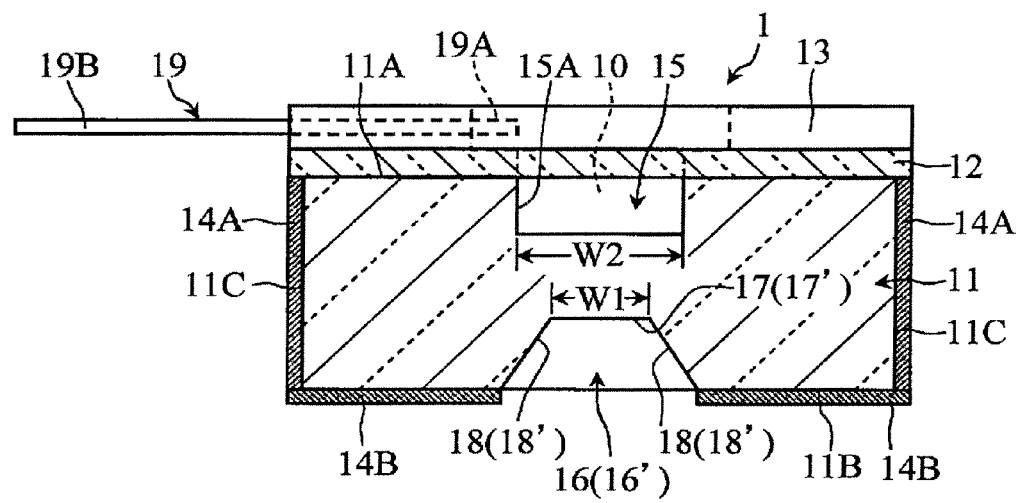
FIG. 4 is a cross-sectional view along a line IV-IV in FIG. 1.
Figure 5:
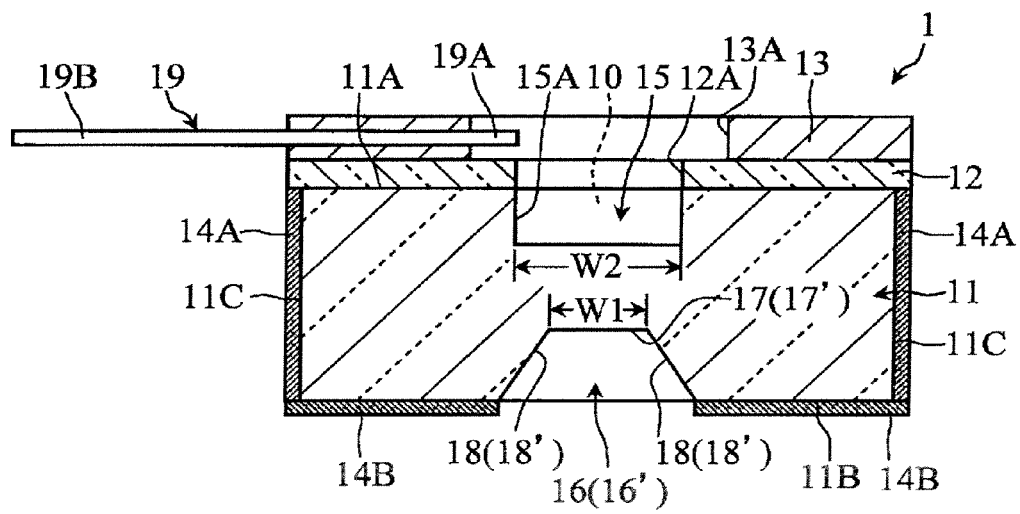
FIG. 5 is a cross-sectional view along a line V-V in FIG. 1.

As shown in FIG. 4 and FIG. 5, the light go-through surfaces 17, 17' allow light flux emitted from the flow channel 10 to go therethrough. In the aperture 16 shown in FIG. 3A, the light go-through surface 17 is formed as a flat surface extending in the lengthwise direction of the substrate 11 corresponding to the flow channel 10 (the groove 15). A width size W1 of the light go-through surface 17 is smaller than a width size W2 of the flow channel 10 (the groove 15). On the other hand, in the aperture 16' shown in FIG. 3B, the light go-through surface 17' is formed as a circular flat surface facing the flow channel 10 (the groove 15). A diameter W1 of the light go-through surface 17' is smaller than the width size W2 of the flow channel 10 (the groove 15).

The light reflective surfaces 18, 18' totally reflect light flux emitted from the flow channel, and cause such light flux to go toward a side face 11C of the substrate 11. The pair of light reflective surfaces 18 shown in FIG. 3A faces with each other and is provided as flat surfaces inclined with respect to an optical axis L of light flux. The light reflective surfaces 18 are formed so as to have a clearance made wider as being apart from the flow channel 10, and an inclination angle of the light reflective surface is set to be an angle that causes light flux which has reached the light reflective surface 18 to totally reflect. On the other hand, the light reflective surface 18' shown in FIG. 3B is formed in a conical shape so that a space thereof becomes wide as being apart from the light go-through surface 17'. Like the light reflective surface 18 (see FIG. 3A), an inclination angle of the light reflective surface 18' is set to be an angle that causes light flux which has reached the light reflective surface to totally reflect.

Now, a condition in which light flux can reflect the light reflective surface 18, 18' will be discussed. In the light reflective surface 18, 18', a critical angle θm which causes a total reflection satisfies a relationship $\sin θm = n1/n2$ (where $n2>n1$). n1 is a refractive index of air, and n2 is a refractive index of a substrate 1. In this case, if the refractive index n1 of air is 1, conditions satisfied between a material of the substrate 11 and the critical angle θm are shown in table 1 below.

TABLE 1

| Material | Refractive Index n2 | Critical Angle θm |
|---|---|---|
| PDMS | 1.45 | 43.6 degree |
| PMMA | 1.49 | 42.2 degree |
| PS | 1.59 | 39.0 degree |
| PC | 1.59 | 39.0 degree |

In the table 1, PDMS is a silicone resin, PMMA is a methyl methacrylate resin (acrylate resin), and PC is a polycarbonate resin.

Note that the refractive index differs depending on a wavelength, but θm can be set based on a refractive index in a maximum wavelength of the wavelength used.

Figure 6:
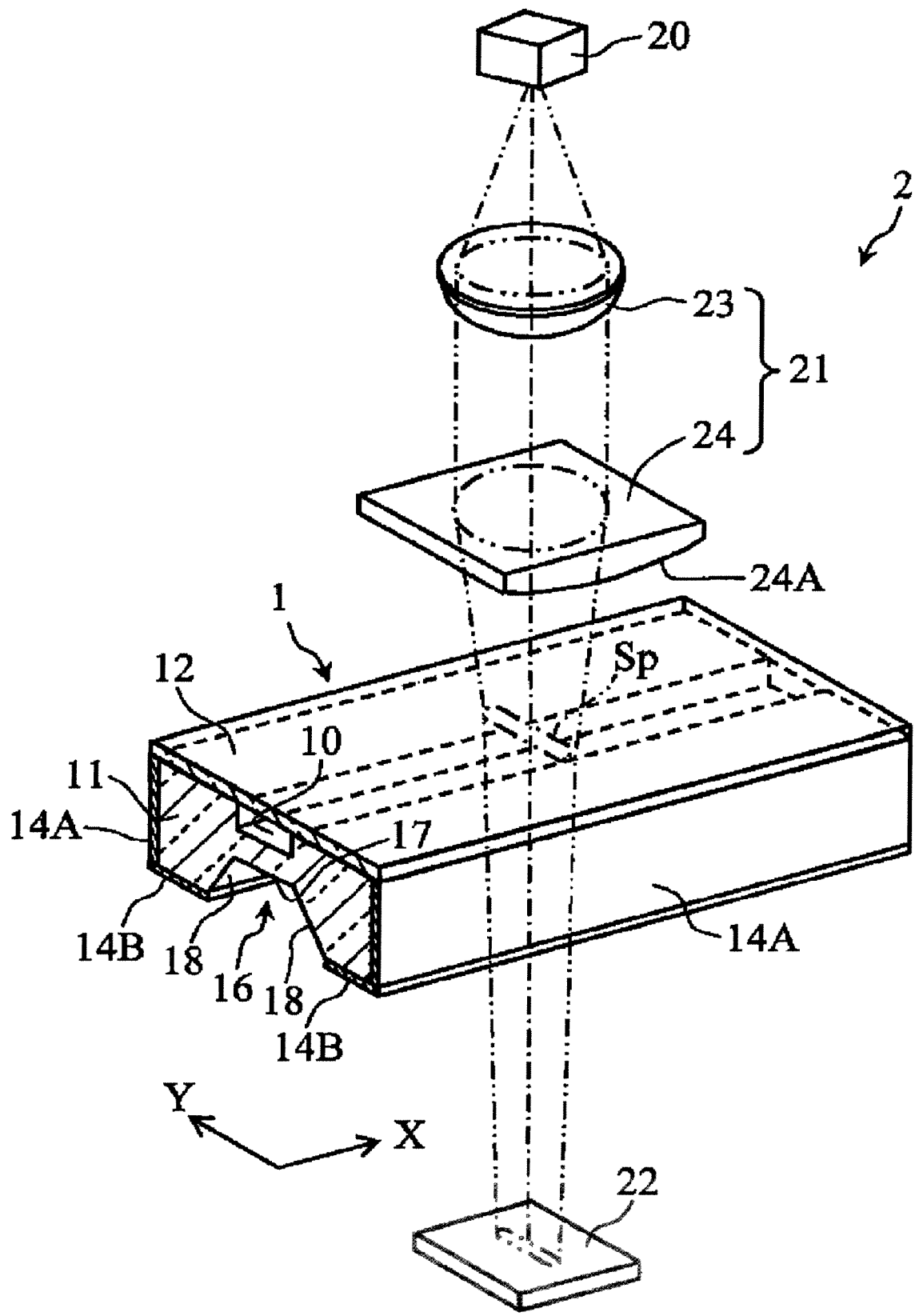
FIG. 6 is a perspective view showing a general structure of an analyzing apparatus according to the present invention.
Figure 7:
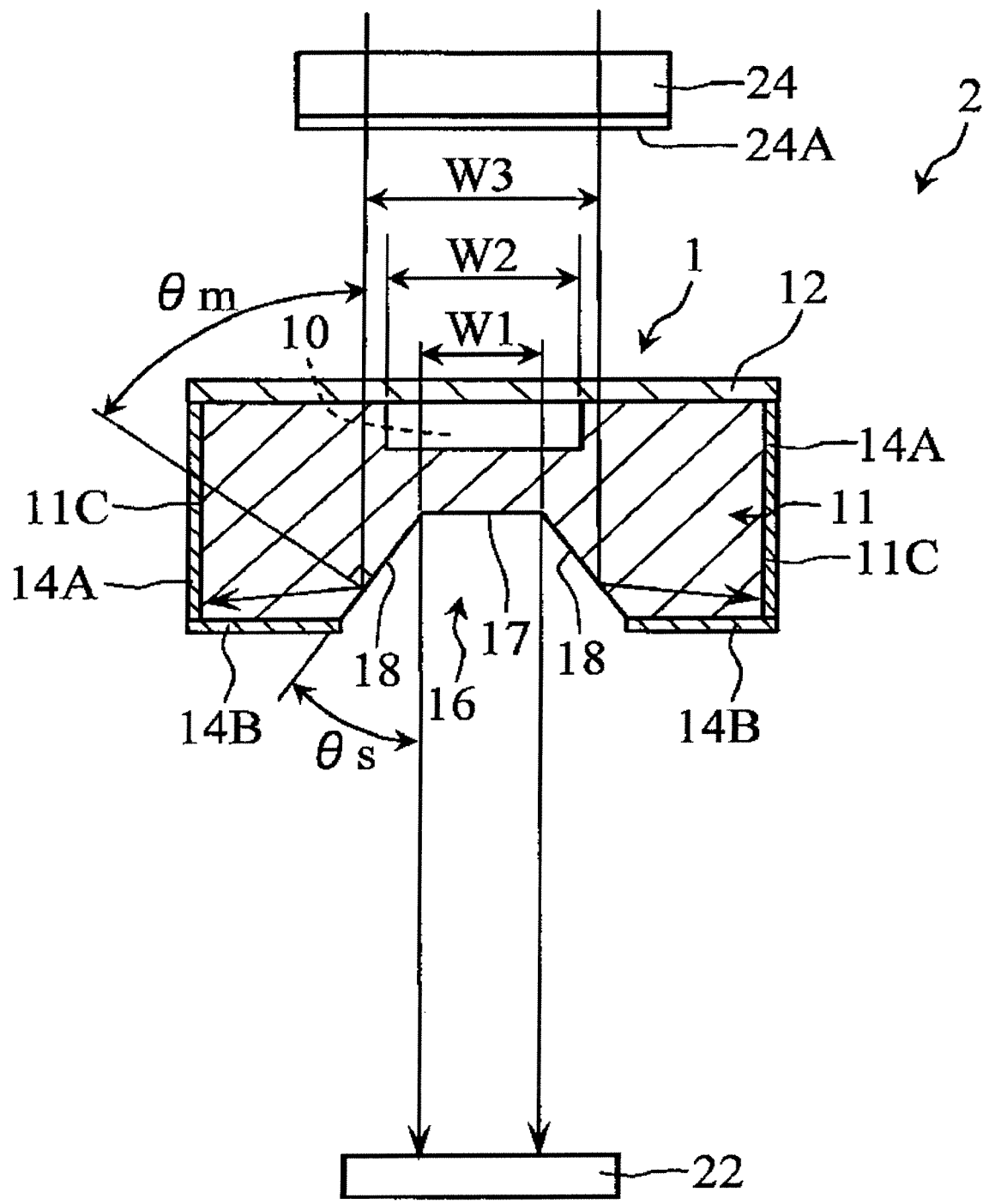
FIG. 7 is a cross-sectional view of the analyzing apparatus shown in FIG. 6.

Like an analyzing apparatus 2 shown in FIG. 6 and FIG. 7, when incident light on the microchip 1 is parallel light as viewed from an X directional, the inclination angle θs of the light reflective surfaces 18, 18' becomes $θs<90-θm$. For example, when the material of the substrate 1 is PDMS, the critical angle θm becomes 43.6 degree. Therefore, when the material of the substrate 1 is PDMS, the inclination angle θs of the light reflective surface 18 can be set to be equal to or less than 46.4 degree.

The cover 12 defines the flow channel 10 together with the substrate 11, and is formed of a transparent material. The cover 12 is formed in a tabular shape with the same material as that of the substrate 11, and covers the groove 15 of the substrate 11. The cover 12 has through-holes 12A, 12B provided at positions corresponding to ends 15A, 15B, respectively. These through-holes 12A, 12B are communicated with the groove 15 and respective through-holes 13A, 13B of a tabular member 13 to be described later, and form an inlet 10A and an outlet 10B.

The tabular member 13 defines the inlet 10A for a migration solution to be supplied to the flow channel 10 and the outlet 10B, and for holding an electrode 19. The tabular member 13 has the through-holes 13A, 13B which form the inlet 10A and the outlet 10B, respectively. The electrode 19 applies a voltage to the migration solution to the flow channel 10, and to the migration solution filled in the flow channel 10 to make the samples separated by electrophoresis. An end 19A of the electrode 19 protrudes in the through-holes 13A, 13B (the inlet 10A and the outlet 10B) of the tabular member 13, and is formed so as to contact the migration solution. An end 19B of the electrode 19 protrudes laterally from the tabular member 19, and is connected to a non-illustrated power supply source.

The shading members 14A, 14B prevent light from being emitted from portions other than the apertures 16, 16'. The shading member 14A prevents light from being emitted from a side face 11C of the substrate 11, and is provided at the side face 11C of the substrate 11. The shading member 14B prevents light from being emitted from the lower face 11B of the substrate 11, and is provided in the vicinity of the apertures 16, 16' in the lower face 11B of the substrate 11. The shading members 14A, 14B can be formed by, for example, applying, stamping or printing a coating material which absorbs light with a measurement-wavelength, or pasting a film including a colorant or a pigment which absorb light with a measurement-wavelength.

According to the microchip 1 with such a structure, the migration solution is applied from the inlet 10A toward the flow channel 10, and further, the sample is applied. Next, by applying a voltage across the two electrodes 19, the sample is subjected to electrophoresis and is separated. The separated sample is analyzed by irradiating the sample with light. For this analysis, for example, absorptiometric method or fluorometry is adopted.

An illustrative analyzing apparatus according to the present invention will be explained below with reference to FIG. 6 and FIG. 7. However, in the following explanation, an explanation will be given of an example case in which the microchip 1 shown in FIG. 3A is used.

The analyzing apparatus 2 shown in FIG. 6 analyzes the sample using the microchip 1 which is mounted in a non-illustrated mount part, and has a light source 20, an optical system 21 and a detection unit 22.

It is appropriate if the mount part employs a structure that enables positioning of the microchip 1. The detail thereof will be explained later, but it is desirable that the precision of position be high precise, but a strict precision is not requisite. Moreover, a mechanism which adjusts the position of the mount part is not particularly needed. An example of the mount part is a tray with a concave recess which engages with the contour of the microchip 1, and the aperture size of the concave portion may be slightly larger than the overall size of the microchip 1.

The light source 20 irradiates the predefined location of the flow channel 10 in the microchip 1 with light. An example of the light source 20 is a laser, a LED or an optical fiber.

The optical system 21 guides the lights emitted from the light source 20 to the predefined location of the flow channel 10. The optical system 21 has a collimated lens 23 and a cylindrical lens 24.

The collimated lens 23 causes diverging light emitted from the illuminant 20 to be parallel light.

The cylindrical lens 24 causes light flux which was made as parallel light in the collimated lens 23 to be converged. The cylindrical lens 24 has a light go-through surface 24A made as a convex curved surface, and is arranged in such a way that light flux which has passed through the cylindrical lens 24 is converged in the lengthwise direction (X direction) of the flow channel 10, but not converged in the widthwise direction (Y direction) of the flow channel 10. Therefore, light flux having passed through the cylindrical lens 24 is made as light flux that is a spot Sp emitted to the microchip 1 (the cover 12 and the flow channel 10) and having a long axis in the short direction (X direction) of the substrate 11 (the flow channel 10). The spot Sp goes across the flow channel 10, and the length of the long-axis direction (Y direction) is longer than the width of the flow channel 10.

The detection unit 22 receives light which has passed through the microchip 1, and generates an electrical signal in accordance with an amount of received light. The electrical signal corresponds to an amount of target element in the sample, and the sample can be analyzed based on the electrical signal.

In the analyzing apparatus 2, diverging light emitted from the light source 20 is made as parallel light through the collimated lens 23, is converged through the cylindrical lens 24, and is emitted to the microchip 1 as the spot Sp which has the long axis in the direction that intersects the flow channel 10 of the microchip 1.

The light flux emitted to the microchip 1 passes through the cover 12, and enters into the substrate 11. At this time, the light flux which passes through the flow channel 10 is emitted to the sample separated by electrophoresis. Most of the light flux which passes through the flow channel 10 enters into the aperture 16, and light which does not enter into the aperture 16 is absorbed in the shading member 14B.

Some of the light flux entered into the aperture 16 passes through the light go-through surface 17, and the rest is totally reflected in the light reflective surface 18. The light totally reflected in the light reflective surface 18 travels toward the side face 11C of the substrate 11. The light which has reached the side face 11C of the substrate 11 is absorbed in the shading member 14A.

On the other hand, light flux which has passed through the light go-through surface 17 is received by the detection unit 22, and is used to analyze the sample. A spot Sp formed in the detecting unit 22 is shorter in both width (X direction) and length (Y direction) than the spot Sp formed in the microchip 1. The reason why the width (X direction) of the spot Sp formed in the detecting unit 22 is short is that a converging action by the cylindrical lens 24 is applied to such a spot.

In contrast, regarding the length (Y direction) of the spot Sp, no converging action by the cylindrical lens 24 affects on it, but the length (Y direction) of the spot Sp becomes short because some of the light flux is blocked in the light reflective surface 18 when passing through the aperture 16. More specifically, as shown in FIG. 7, when the sample is analyzed by the analyzing apparatus 2 using the microchip 1, light flux with a length of L1 which is larger than a width L2 of the flow channel 10 enters into the microchip 1. Because no converging action affects on the light flux by the cylindrical lens 24, such flux travels the substrate 11 while maintaining the length L1, and enters into the aperture 16. The light which has reached the aperture 16 reaches the light go-through surface 17 and the light reflective surface 18. The light which has reached the light go-through surface 17 passes through the light go-through surface 17, and the light which has reached the light reflective surface 18 is reflected. Therefore, by passing through the aperture 16, the light flux becomes light flux with a length W1 which is the width (diameter) of the light go-through surface 17, and reaches the detecting unit 22.

According to this structure, light other than the light which has passed through the flow channel 10 does not reach the detecting unit 22, and even the light which has passed through the flow channel 10 and has reached the light reflective surface 18 does not reach the detecting unit 22. That is, only the light which has passed through the light go-through surface 17 is received by the detecting unit 22. In other words, the analytical precision can be improved because it is possible to detect only the light which is necessary to analyze the sample by the light reflective surface 18 of the aperture 16.

Moreover, the light flux which has entered into the microchip 1 and other than the light flux which has passed through the light go-through surface 17 of the aperture 16, is absorbed in the shading members 14A, 14B. Therefore, it is possible for the microchip 1 to prevent the internal stray light which is generated in the interior of the microchip 1 from being emitted outside the microchip 1 by providing the shading members 14A, 14B. As a result, the analytical precision can be improved because it is possible to suppress a reception of unnecessary light in the detecting unit 22.

Moreover, according to the present invention, the setting precision of the microchip 1 can be obtained when not being strict. That is, when the sample is analyzed using the microchip 1, the microchip 1 is mounted at the mount part (not shown) of the analyzing apparatus 2. Where the mount part is the tray with the concave recess, an aperture of the concave recess is set to be slightly larger than the overall size of the microchip 1 in consideration of the varying of the overall size of the microchip 10. The structure can cope with the varying of the overall size of the microchip 1, but the installed position of the microchip 1 may vary.

On the other hand, the spot Sp of the microchip 1 intersects the flow channel 10. In this case, if the microchip 1 moves in the lengthwise direction (X direction) of the flow channel 10, there is no change in the state in which the spot Sp and the flow channel 10 intersect with each other. On the other hand, the length (Y direction) of the spot Sp is larger than the width of the flow channel 10. This enables the spot Sp and the flow channel 10 to keep the intersected state even if the microchip 1 moves in the width direction (Y direction) of the flow channel 10.

That is, even if the position of the microchip 1 is changed, the analytical precision can be maintained the spot with a length L3 which has passed through the flow channel 10 reaches the detecting unit 22 as far as the spot Sp and the flow channel 10 are intersected with each other.

Therefore, the analytical precision can be ensured if the microchip 1 is used to analyze the sample by forming the aperture 16 in the microchip 1 without making the precision of the positioning of the microchip 1 strict, and without providing a position adjusting mechanism separately. The aperture 16 can be formed together with the substrate 11, and needs no particular additional component. That is, according to the microchip 1, while accepting the positional varying, the analytical precision for the sample can be ensured with a simple structure. Such an effect can also be obtained in the same way when the microchip 1 shown in FIG. 3B is used.

Needless to say, the present invention can be changed and modified in various forms. For example, in the optical system 21, the cylindrical lens 24 which is used to form the vertically long spot Sp in the microchip 1 is used, but instead of this lens, an aperture which has a vertically long slit may be arranged.

Figure 8:
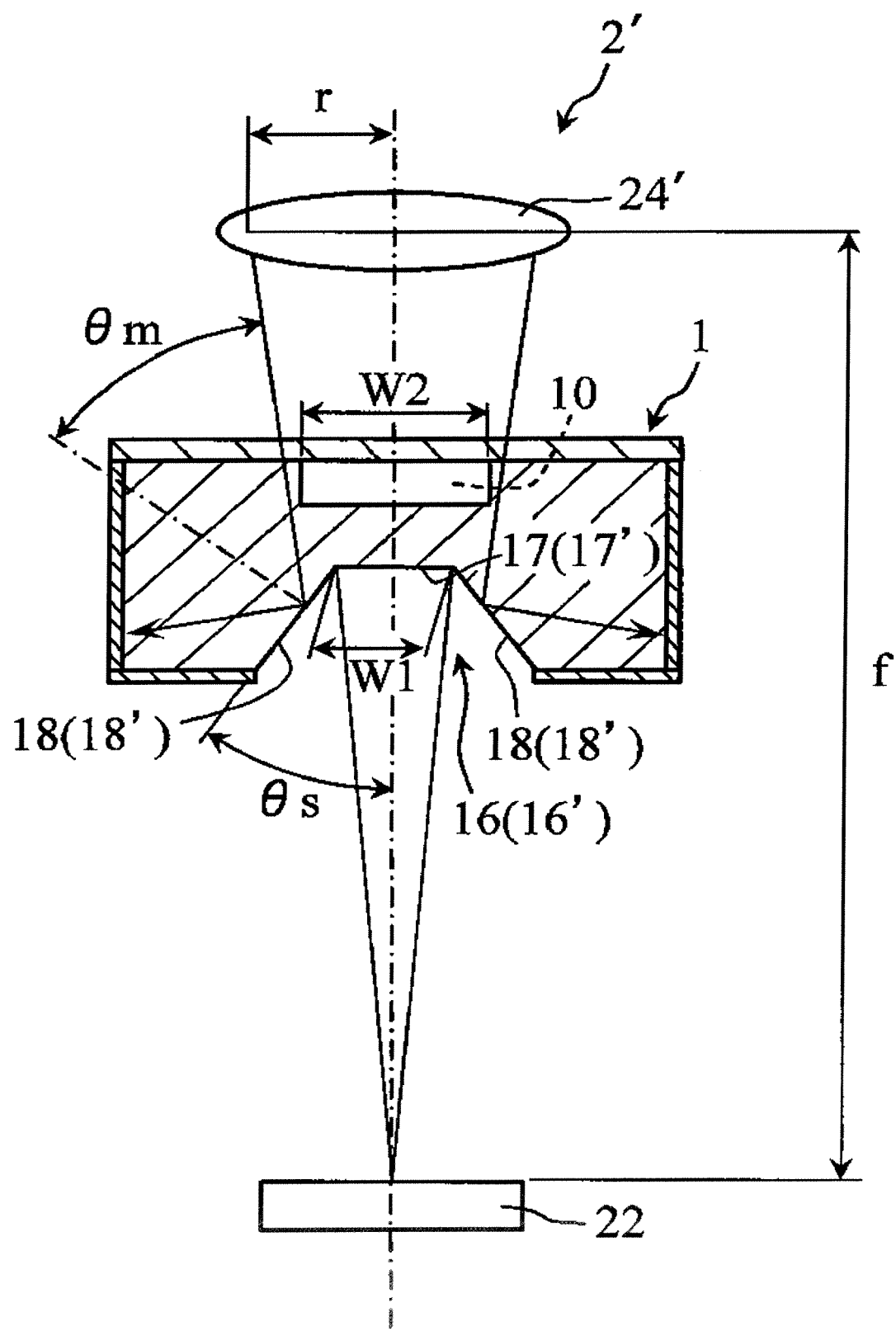
FIG. 8 is a cross-sectional view showing another illustrative analyzing apparatus according to the present invention.

Like an analyzing apparatus 2' shown in FIG. 8, it is also possible to make light flux converged in the width direction (Y direction) of the flow channel 10 by using a light condenser lens 24' instead of the cylindrical lens 24.

According to the structure shown in FIG. 8, also, circular light flux with a diameter which is larger than the width W2 of the flow channel 10 enters into the microchip 1. This light flux travels the substrate 11 while being converged. The light condenser lens 24' is set so as to maintain a state in which the light flux and the flow channel 10 are intersected with each other while the light flux passes through the flow channel 10.

Some of the light which has reached the aperture 16 (16') passes through the light go-through surface 17, while at the same time, the rest is reflected by the light reflective surface 18 (18'). Therefore, as the light flux passes through the aperture 16 (16'), the light flux in the light go-through surface 17 (17') is converged and reaches the detecting unit 22. The analytical precision can be improved because no light other than the light which has passed through the flow channel 10 reaches the detecting unit 22. Such an effect can also be accomplished even if the positioning precision of the microchip 1 is not made strict.

Now, a condition in which the light flux can totally reflect the light reflective surface 18 (18') will be discussed. The critical angle θm which causes the total reflection at the light reflective surface 18 (18') satisfies the relationship sin θm=n1/n2 (where n2>n1). n1 is the refractive index of air, and n2 is the refractive index of the substrate 1. In this case, if the refractive index n1 of air is 1, conditions satisfied between a material of the substrate 1 and the critical angle θm are as shown in the foregoing table 1.

When the light condenser lens 24' is used like the analyzing apparatus 2' shown in FIG. 8, an angle θs can be set in consideration of an incident angle of incident light. The incident angle θs of the incident light satisfies θs<(90−θm)−α(tan α=r/f). r is an effective radius of the light condenser lens 24', and f is a focal length of the light condenser lens 24'.

For example, when the material of the substrate 11 is PDMS, the critical angle θm is 43.6 degree. Therefore, when the material of the substrate 11 is PDMS, the inclination angle θs of the light reflective surface 18 (18') can be set to be equal to or less than 19.8 degree in a case in which the effective radius r of the light condenser lens 24' is 5 mm and the focal length f thereof is 10 mm.

Moreover, it is possible for the microchip of the present invention to change and modify the shading member in various forms.

Figure 9:
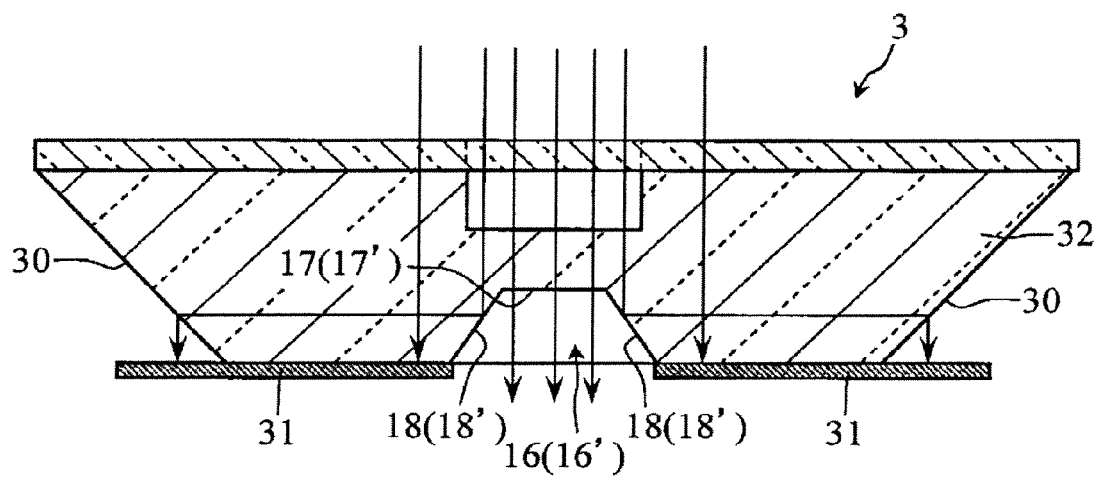
FIG. 9 is a cross-sectional view showing another illustrative microchip according to the present invention.
Figure 10:
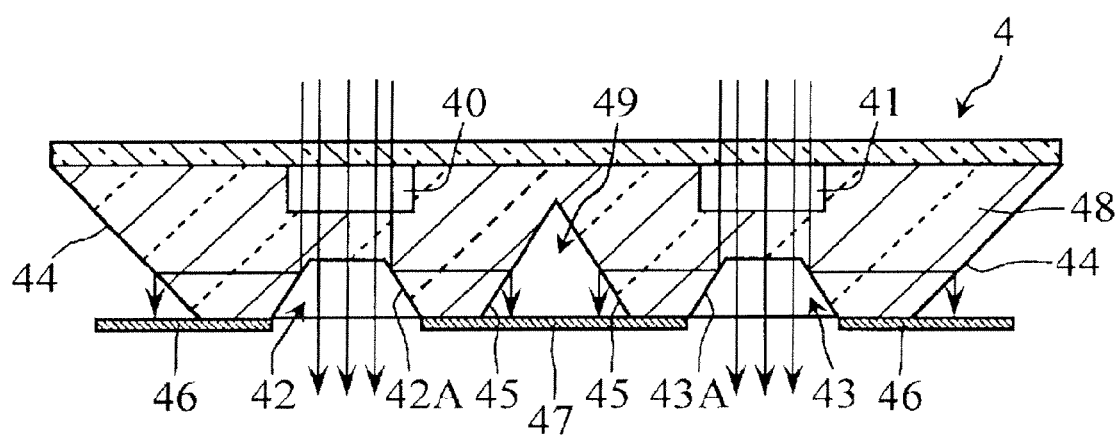
FIG. 10 is a cross-sectional view showing the other illustrative microchip according the present invention.

The shading member 14A, 14B are unnecessary in some cases, one or both of the shading members 14A, 14B can be omitted, or it is possible to employ structures shown in FIG. 9 and FIG. 10 as the shading member.

A microchip 3 shown in FIG. 9 has a guide surface 30 and a shading member 31.

The guide surface 30 guides light flux which has been totally reflected by the light reflective surface 18 (18') of the aperture 16 (16') to the exterior of a substrate 32. The guide surface 30 is formed by causing a side face of the substrate 32 to be an inclined surface.

The shading member 31 absorbs the light flux which has been guided to the exterior of the substrate 32 by the guide surface 30, and protrudes toward the side of the substrate 32. The shading member 31 is formed by pasting up an absorption member like a film containing a colorant or a pigment which absorbs light with an analytical wavelength on a lower face 33 of the substrate 32.

According to the microchip 3, light flux which has been totally reflected by the reflective surface 18 (18') of the aperture 16 (16') travels toward the side face 30 (the guide surface) of the substrate 32. This light flux is turned downwardly at the side face 30 (the guide surface), and is emitted from the side face 30 (the guide surface). The light flux emitted from the guide surface 30 is absorbed by the shading member 31.

A microchip 4 shown in FIG. 10 has plural flow channels 40, 41 and plural apertures 42, 43. The plural flow channels 40, 41 are provided adjacent to each other. The apertures 42, 43 are provided right below the flow channels 40, 41, and have the similar form to that of the aperture 16 (16') of the microchip 1 shown in FIG. 3A or FIG. 3B. Further, the microchip 4 has guide surfaces 44, 45 and shading members 46, 47.

The guide surfaces 44, 45 guide light flux which has totally reflected by light reflective surfaces 42A, 43A of the apertures 42, 43 to the exterior of a substrate 48. The guide surfaces 44 are the inclined side face of the substrate 48, and the guide surfaces 45 are formed by providing a V-shaped concave portion 49 between the adjoining apertures 42, 43. That is, in addition to the guide surface 44 which is similar to the guide surface 30 of the microchip 3 shown in FIG. 9, the guide surfaces 44, 45 include the guide surface 45 as an inclined surface which defines the V-shaped concave portion 49.

The shading members 46, 47 absorb light flux guided to the exterior of the substrate 48 by the guide surfaces 44, 45. In addition to the shading member 46 protruding toward the side of the substrate 48 like the shading member 31 of the microchip 4 shown in FIG. 9, the shading members 46, 47 contain the shading member 47 which covers the V-shaped concave portion 49.

Where the microchip 4 has plural flow channels 40, 41, it is possible to appropriately prevent light flux which has passed through one flow channel 40 (41) from entering into the adjoining flow channel 41 (40). That is, light which passes through the one flow channel 40 (41) and travels to the adjoining flow channel 41 (40) is turned downwardly at the guide surfaces (inclined surfaces) 44, 45 of the concave portion 49, and is emitted from the substrate 48. Accordingly, in the adjoining flow channels 40, 41, it is possible to prevent light from entering into the other flow channel 41 (42) from the one flow channel 40 (41).

Furthermore, light which has the direction turned by the concave portion 49 and is emitted from the substrate 48 is absorbed by the shading member 47. Accordingly, the analytical precision can be improved because it is possible to suppress a reception of light which travels from the one flow channel 40 (41) toward the other flow channel 41 (40) by the detecting unit 22.

Moreover, in the analyzing apparatus of the present invention, a semiconductor laser can be employed as the light source. The semiconductor laser generally emits elliptical laser beam due to its structure. For example, if a VLM visible light laser module (product code: 38927-D) made by Edmond Corporation is used, the beam shape will be 4.0×1.0 mm. When a normal light condenser lens or a collimator is used in order to reduce a spot-size to be 1/20, the spot size becomes 0.2×0.05 mm. By providing the semiconductor laser so as to cause the lengthwise direction of the reduced spot to traverse the flow channel 10, the vertically long spot can be formed in the direction intersects the flow channel 10 like a spot Sp shown in FIG. 6.

Figure 11:
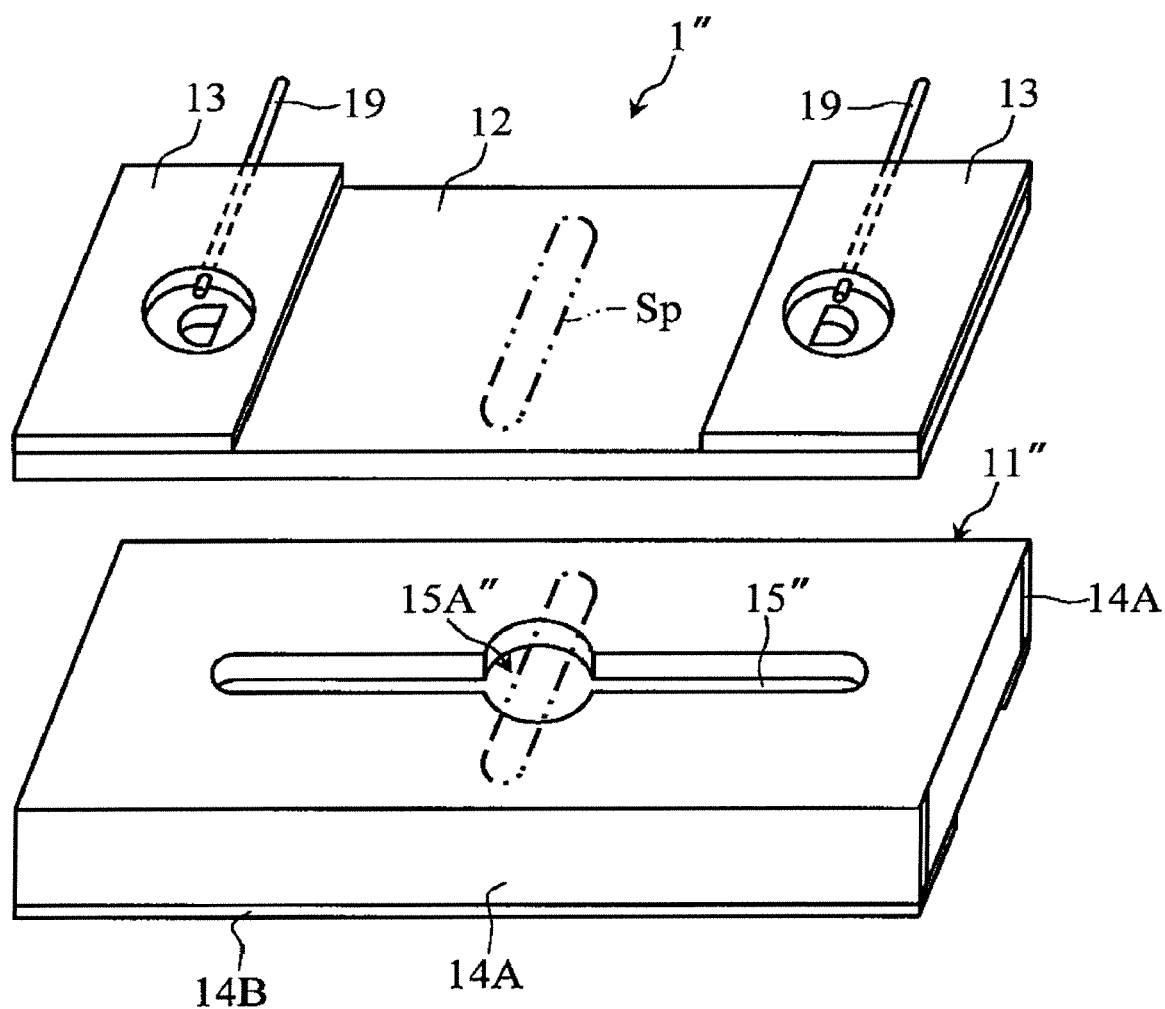
FIG. 11 is an exploded perspective view showing yet other illustrative microchip according to the present invention.
Figure 12:
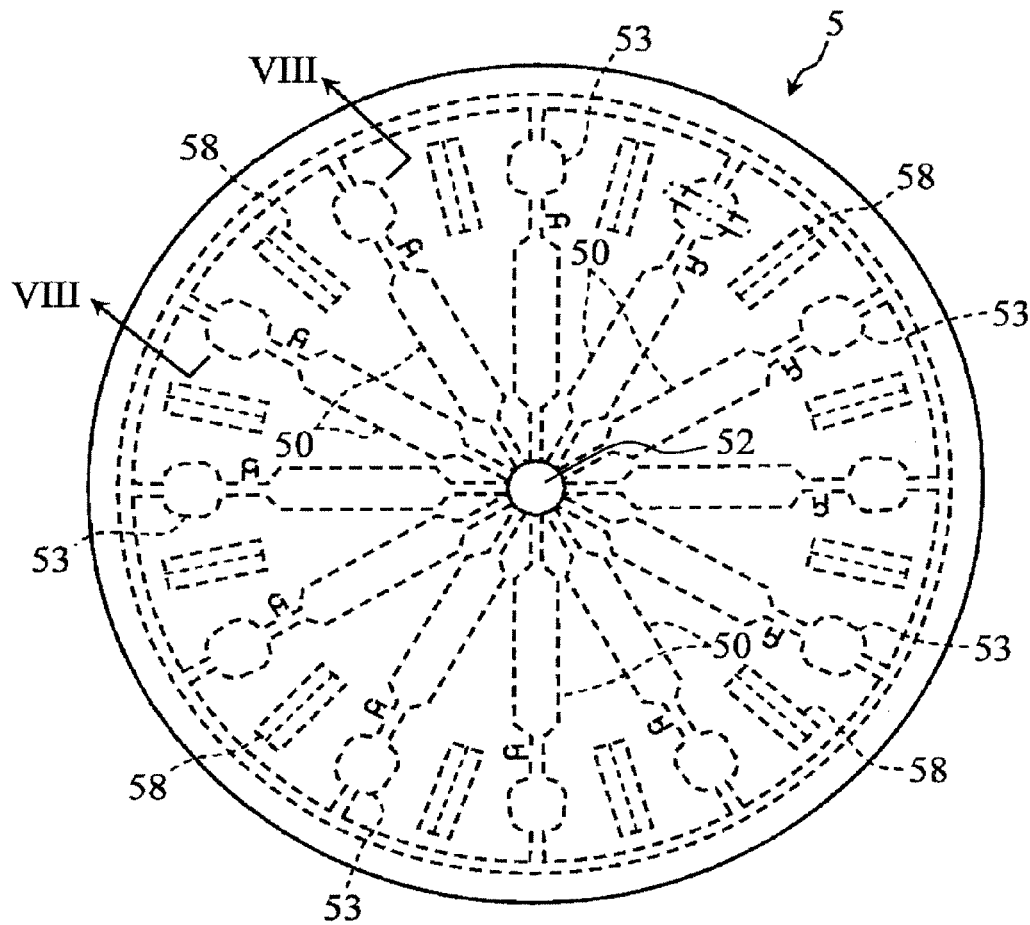
FIG. 12 is a plan view showing a further illustrative microchip according to the present invention.
Figure 13:
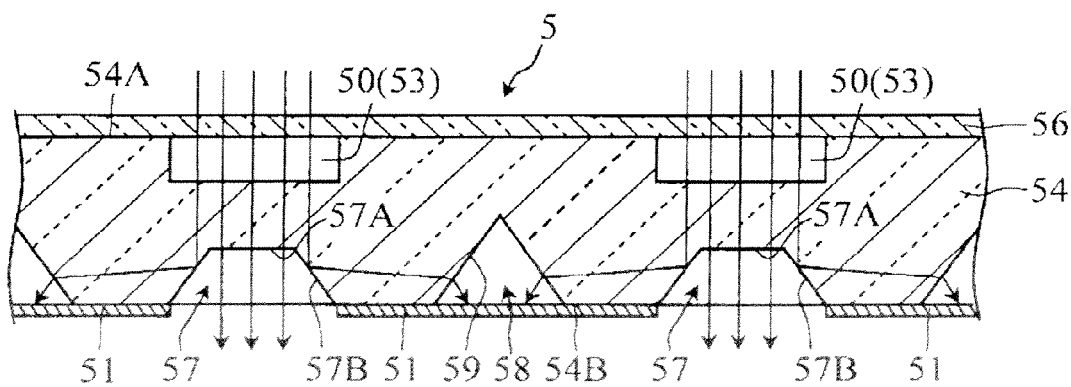
FIG. 13 is a cross-sectional view along a line VIII-VIII in FIG. 12.
Figure 14:
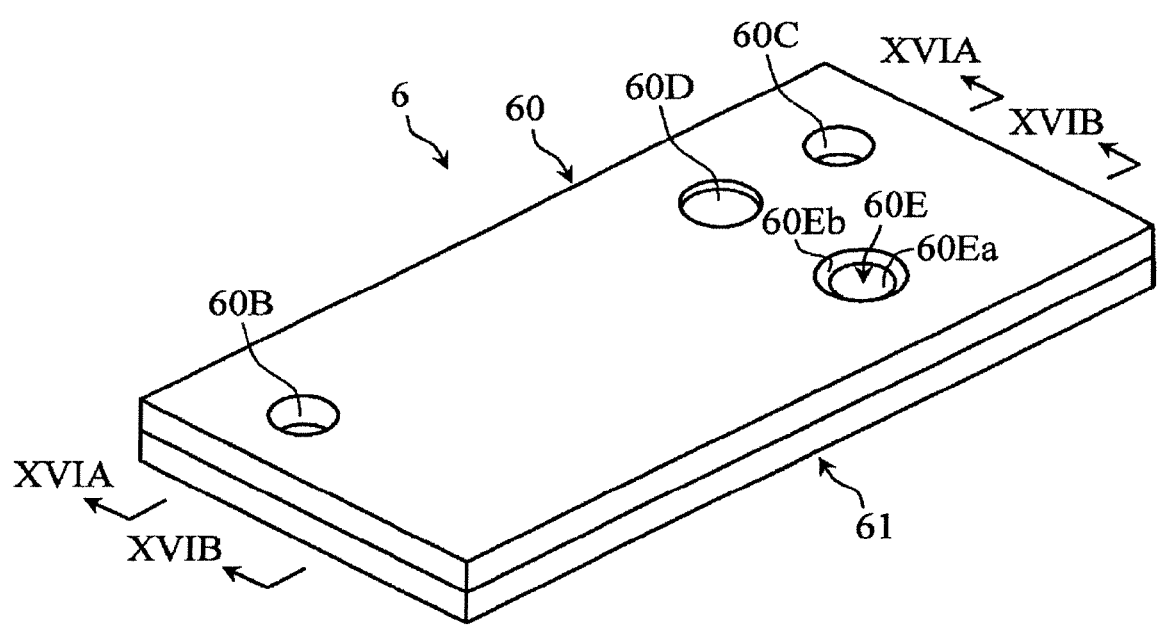
FIG. 14 is a perspective view showing a still further illustrative microchip according to the present invention.
Figure 15:
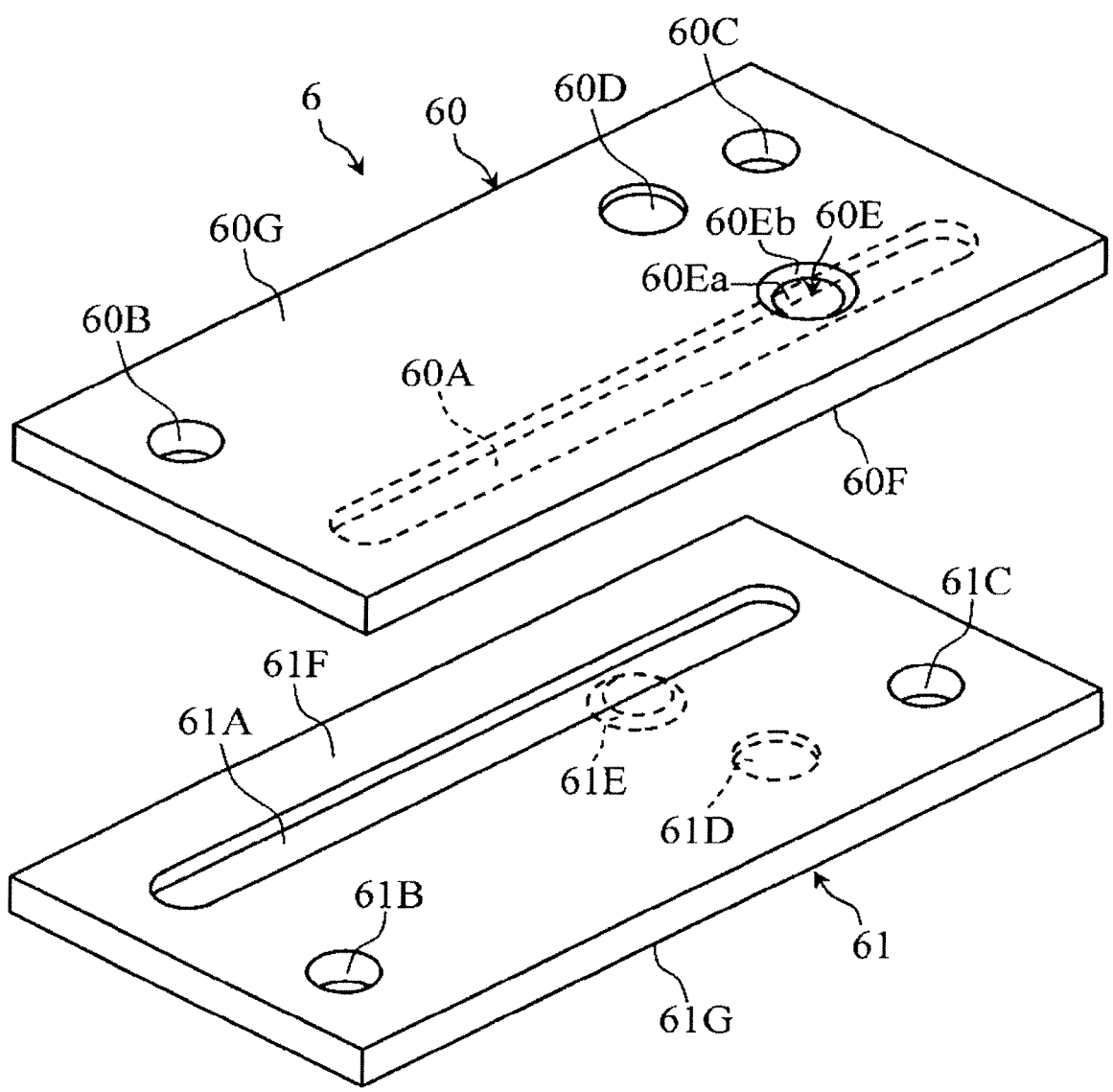
FIG. 15 is an exploded perspective view of the microchip shown in FIG. 14.
Figure 16A:
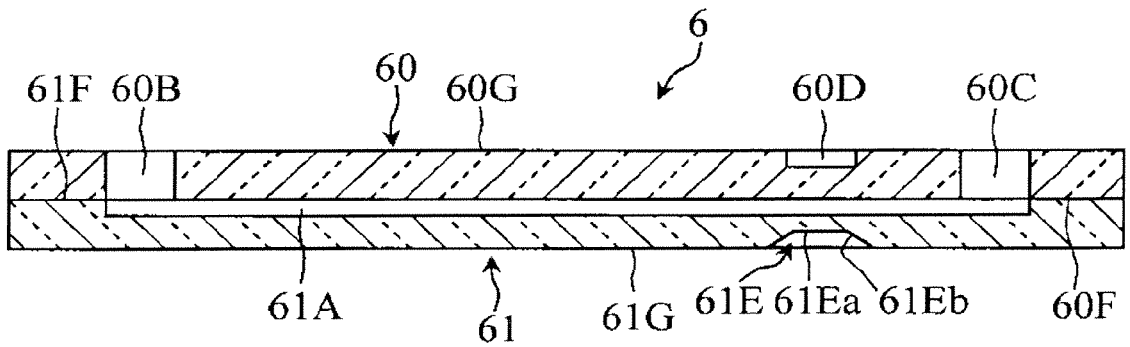
FIG. 16A is a cross-sectional view along a line XVIA-XVIA in FIG. 14.
Figure 16B:
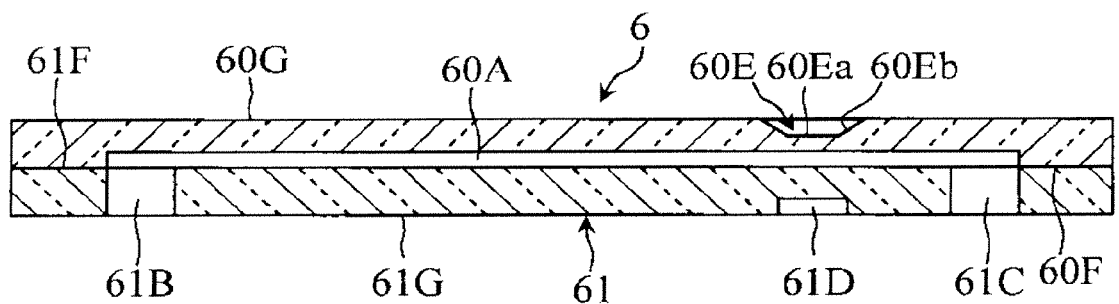
FIG. 16B is a cross-sectional view along a line XVIB-XVIB in FIG. 15.

Moreover, the present invention can be also applied to a microchip 1" shown in FIG. 11, a microchip 5 shown in FIG. 12 and FIG. 13 or a microchip 6 shown FIG. 14 to FIG. 16.

The microchip 1" shown in FIG. 11 is provided with a cell 15A" which is provided in the halfway of a groove 15" that defines the flow channel (a reference numeral 10 of the microchip 1 explained with the reference to FIG. 1 to FIG. 5) in the substrate 11". The cell 15A" has a larger diameter than the width of the groove (flow channel) 15", and is defined by a circular cylindrical concave portion which is formed in the substrate 11". According to such a microchip 1, the cell 15A" is irradiated with light flux so that the light flux intersects the cell 15A".

The microchip 5 shown in FIG. 12 and FIG. 13 is formed in disk shape as a whole, and is provided with plural flow channels 50 and plural shading members 51.

The plural flow channels 50 are formed radially from an inlet 52. Each flow channel 50 is provided with each cell 53. The cells 53 are arranged on the same circumference. According to this structure, samples in the cells 53 successively adjoining to one another can be measured while rotating the microchip 5 around the inlet 52. These flow channels 50 and cells 53 are formed by forming a concave-portion on a top face 54A of a substrate 54, and by stacking a cover 56 on the substrate 54.

A lower face 54B of the substrate 54 is provided with apertures 57 and V-shaped grooves 58.

The aperture 57 is formed right below the cell 53 correspondingly to each cell 53. The aperture 57 is similar to the aperture 16 of the microchip 1 explained with reference to FIG. 1 to FIG. 5, and has a light go-through surface 57A and a pair of light reflective surfaces 57B.

The V-shaped groove 58 is formed so as to be sandwiched between the cells 53 (the aperture 57) and between the adjoining flow channels 50. An inner surface 59 of the V-shaped groove 58 corresponds to the guide surface 45 of the microchip 4 which was explained with reference to FIG. 10, and causes light reflected by the light reflective surface 57B of the aperture 57 to go downwardly of the substrate 54.

The shading member 51 absorbs light which is emitted from an inclined surface (a guide surface) 59 of the V-shaped groove 58, and is formed so as to cover the V-shaped groove 58.

The microchip 6 shown in FIG. 14 to FIG. 16 can measure two samples, and is formed by pasting up a pair of transparent members 60, 61. Each of the transparent members 60, 61 is formed in a long-rectangular tabular shape, and has grooves 60A, 61A, through-holes 60B, 60C, 61B, and 61C and concave portions 60D, 60E, 61D, and 61E.

The groove 60A, 61A define a flow channel together with pasted surfaces 60F, 61F of the other facing transparent members 60, 61. In the pasted surfaces 60F, 61F of individual transparent members 60, 61, the grooves 60A, 61A are formed so as to extend in the lengthwise direction of the transparent members 60, 61. The grooves 60A, 61A are arranged axisymmetric positions in a planar view.

The through-holes 60B, 61B introduce samples into the flow channels (the grooves 60A, 61A), and the through-holes 60C, 61C eject the samples from the flow channels (the grooves 60A, 61A). Such through-holes 60B, 60C, 61B and 61C are formed so as to pass all the way through the transparent members 60, 61 and to be communicated with the ends of the grooves 60A, 61A. The through-holes 60B, 61B are arranged axisymmetric positions in a planar view, and the through-holes 60C, 61C are arranged axisymmetric positions in a planar view.

The concave portions 60D, 61D are used for positioning, and are formed in non-pasted surfaces 60G, 61G in respective transparent members 60, 61. The concave portions 60D, 61D are arranged axisymmetric positions in a planar view.

The concave portions 60E, 61E correspond to the aperture 16' of the microchip 1 shown in FIG. 3B, and have light go-through surfaces 60Ea, 61Ea and conical light reflective surfaces 60Eb, 61Eb. The concave portions 60E, 61E are formed right below the groove 60A and right below the groove 61A of the facing transparent members 60, 61, respectively. The concave portions 60E, 61E are arranged axisymmetric positions in a planar view.

The microchip 6 is formed by pasting up the transparent members 60, 61 with respective pasted surfaces 60F, 61F facing each other. Therefore, the microchip 6 has the two flow channels (the grooves 60A, 61A), and have the same structure back and forth. Therefore, it is possible to measure two samples by using the microchip 6 having the front and the back inverted.

In the microchip 6, the pair of grooves 60A and 61A, the pair of through-holes 60B and 61B, the pair of through-holes 60C and 61C, the pair of concave portions 60D and 61D, and the pair of concave portions 60E and 61E may be arranged so as to be point-symmetrical positions, respectively.

A microchip according to the present invention may employ a structure which causes a sample to travel by capillaries of a flow channel, and is not limited to a structure which causes the sample to travel by voltage application like the microchip 1 shown in FIG. 1 to FIG. 5.

Figure 17:
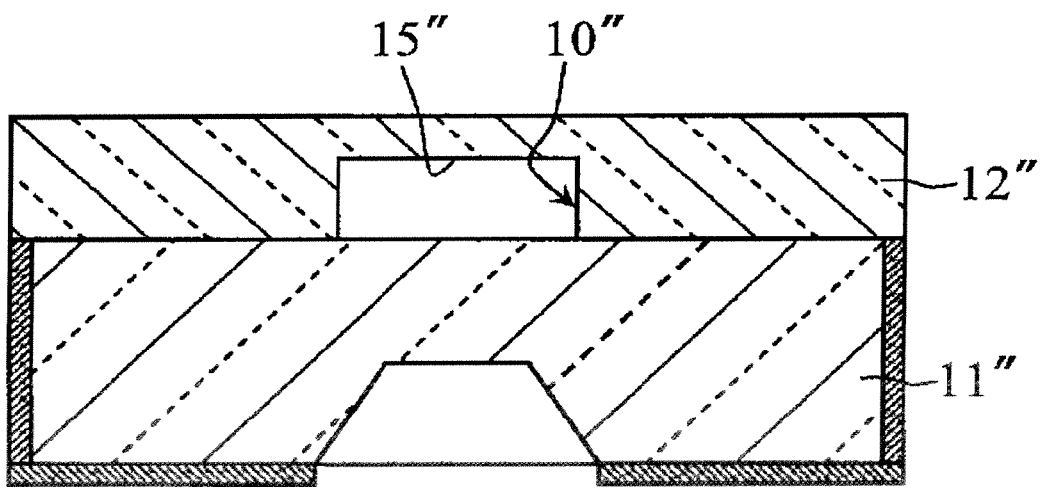
FIG. 17 is a perspective view showing a yet further illustrative microchip according to the present invention.

Moreover, as shown in FIG. 17, a concave portion (a groove) 15" which defines a flow channel 10" and a cell may be formed in a cover 12" not in the substrate 11".

Furthermore the light go-through surface and the light reflective surface of the aperture are not limited to a flat surface, but all of or a part of such surfaces may be a curved surface.

Still further, the optical systems 21 21' in the above-explained analyzing apparatuses 2, 2' are merely examples, and can be designed by combining various lenses, apertures, etc., accordingly.

A second embodiment of the present invention will be explained below with reference to FIG. 18 to FIG. 21.

Figure 18:
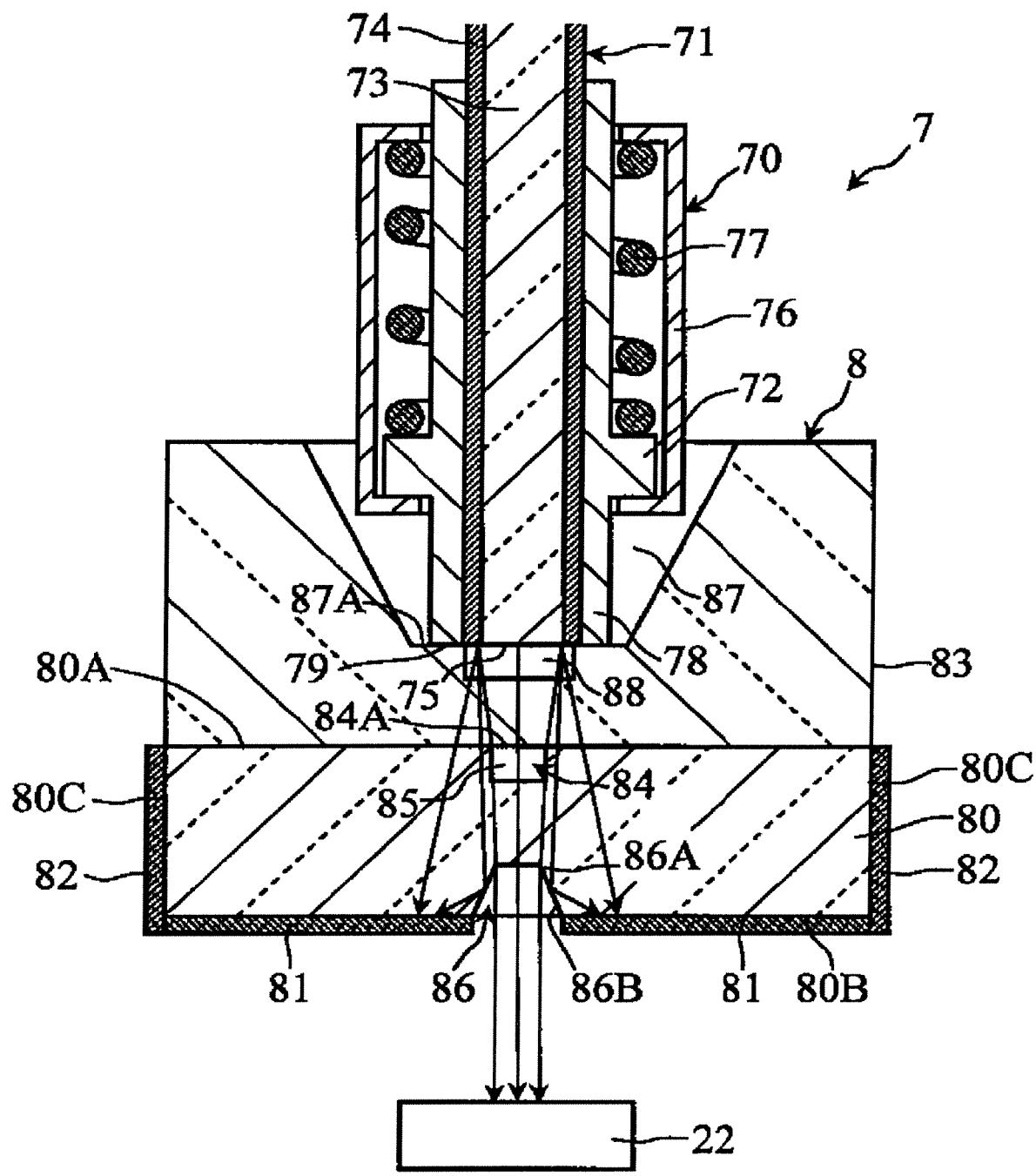
FIG. 18 is a cross-sectional view showing the other illustrative analyzing apparatus according to the present invention.
Figure 19:
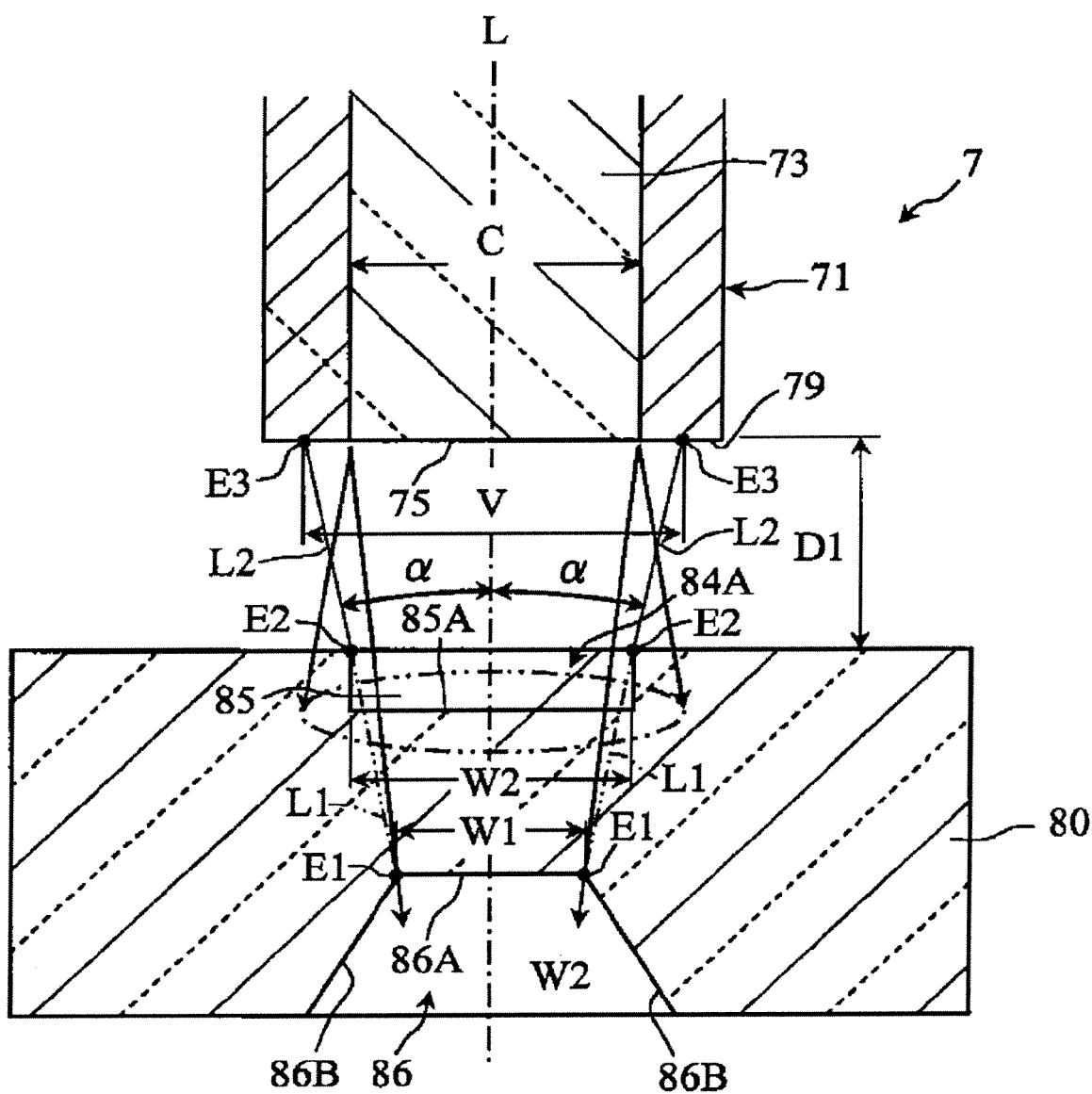
FIG. 19 is a cross-sectional view showing a major part of the analyzing apparatus shown in FIG. 18 being enlarged.

An analyzing apparatus 7 shown in FIG. 18 and FIG. 19 analyzes a sample using a microchip 8, and has irradiating means 70 and a detecting unit 22.

The irradiating means 70 irradiates a flow channel 84 (or a cell) of the microchip 8 with light. This irradiating means 70 has an optical fiber 71 and a ferrule 72.

The optical fiber 71 guides light emitted from a non-illustrated light source to the microchip 8. The optical fiber 71 has a core 73 and a clad 74. The core 73 is a part where the light travels. The clad 74 totally reflects the light at an interface between the core 73 and the clad 74. The clad 74 is formed of a material having a refractive index higher than that of the core 73, and covers the core 73. That is, in the optical fiber 71, light is guided within the interior of the core 73 while repeating total reflection at the interface between the core 73 and the clad 74, and the light is emitted from an end face 75 of the core 73. Light which is emitted from the end surface 75 is light with a numerical aperture corresponding to a total reflective critical angle at the interface between the core 73 and the clad 74, and the light travels while spreading light flux as becoming apart from the end surface 75.

The ferrule 72 holds the end of the optical fiber 71. This ferrule 72 is, in a holder 76, maintained so to be movable in the vertical direction in a condition biased by a coil spring 77. That is, the optical fiber 71 is configured to abut a concave portion 87 of the microchip 8 with appropriate pressing force.

The detecting unit 22 is similar to the detecting unit 22 of the analyzing apparatus 2 explained with reference to FIG. 6 and FIG. 7, and generates an electrical signal in accordance with an amount of received light.

The basic structure of the microchip 8 is similar to that of the microchip 1 explained with reference to FIG. 1 to FIG. 5, and has a substrate 80, shading members 81, 82 and a cover 83.

The substrate 80 has a groove 85 which defines the flow channel 84 (or a cell) and an aperture 86. Respective structures of the groove 85 and the aperture 86 are similar to those of the groove 15 and the aperture 16 of the microchip 1 explained with reference to FIG. 1 to FIG. 5. However, a width size W1 of a light go-through surface 86A of the aperture 86 is smaller than a width size W2 of a bottom face 85A of the groove 85. Therefore, light flux which is smaller than the size of the end surface 75 of the core 73 (a core diameter C) in the optical fiber 71 is permitted to enter into the light go-through surface 86A. Accordingly, it is possible to efficiently eliminate the effect of stray light by adjusting a distance between the end surface 75 of the core 73 and a top face 84A of the flow channel 84 (or the cell) as needed depending on the core diameter C.

The shading members 81, 82 prevent light from being emitted from other than the light go-through surface 86A in the aperture 86 to the exterior of the substrate 80. The shading member 81 is provided adjacent to the aperture 86 in a lower face 80B of the substrate 80. The shading member 82 is provided in a side face 80C of the substrate 80.

The cover 83 is stacked on the substrate 80 so as to cover the groove 85, and defines the flow channel 84 (or the cell) together with the groove 85. The cover 83 has concave portions 87, 88. The concave portion 87 is to be a portion where an end 78 of the irradiating means 70 is arranged, and a bottom face 87A is arranged on the same axis or substantially same axis with the light go-through surface 86A of the aperture 86. In a condition in which the end 78 of the irradiating means 70 is arranged in the concave portion 87, a light go-through end surface 79 of the optical fiber 71 abuts the bottom face 87A of the concave portion 87, or is engaged with the end 78 including the light go-through end surface 79 of the optical fiber 71. The concave portion 88 is provided at the bottom face 87A of the concave portion 87. The concave portion 88 prevents the end surface 75 of the core 73 of the optical fiber 71 from contacting the bottom face 87A of the concave portion 87. By providing such a concave portion 88, the end surface 75 of the core 73 is prevented from being damaged, and it becomes possible to allow desired light flux to be emitted from the end surface 75 repeatedly.

According to a structure which allows the end surface 75 of the optical fiber (the core 73) to abut the bottom surface 87A of the concave portion 87, the position of the bottom surface 87A of the concave portion 87 and the position of the end surface 75 of the core 73 are substantially consistent with each other. In this case, the bottom surface 87A of the concave portion 87 is formed at a position satisfying a relationship C<V. C is the core diameter of the optical fiber 71. V is a size in the light go-through end surface 79 of the optical fiber 71 corresponding to a view angle α of the flow channel 84 (or the cell). The view angle α is defined based on the shape of the light go-through surface 86A in the flow channel 84 (the groove 85 of the substrate 80) and in the aperture 86, and the position of the light go-through surface 86A therein. The view angle α is equivalent to an intersectional angle between a straight line L1 which interconnects an edge E1 of the light go-through surface 86A in the aperture 86 and the edge E2 of the flow channel 84 (or the cell) at the top-face-84A side and an optical axis L. Therefore, the size V is equivalent to a distance between intersections E3, E3 where an extension line L2 of the straight line L1 and the light go-through end surface 79 of the optical fiber 71 intersect with each other, and depends on a position (a distance D between the top face 84A of the flow channel 84 (or the cell)) of the light go-through end surface 79 in the optical fiber 71.

Figure 20:
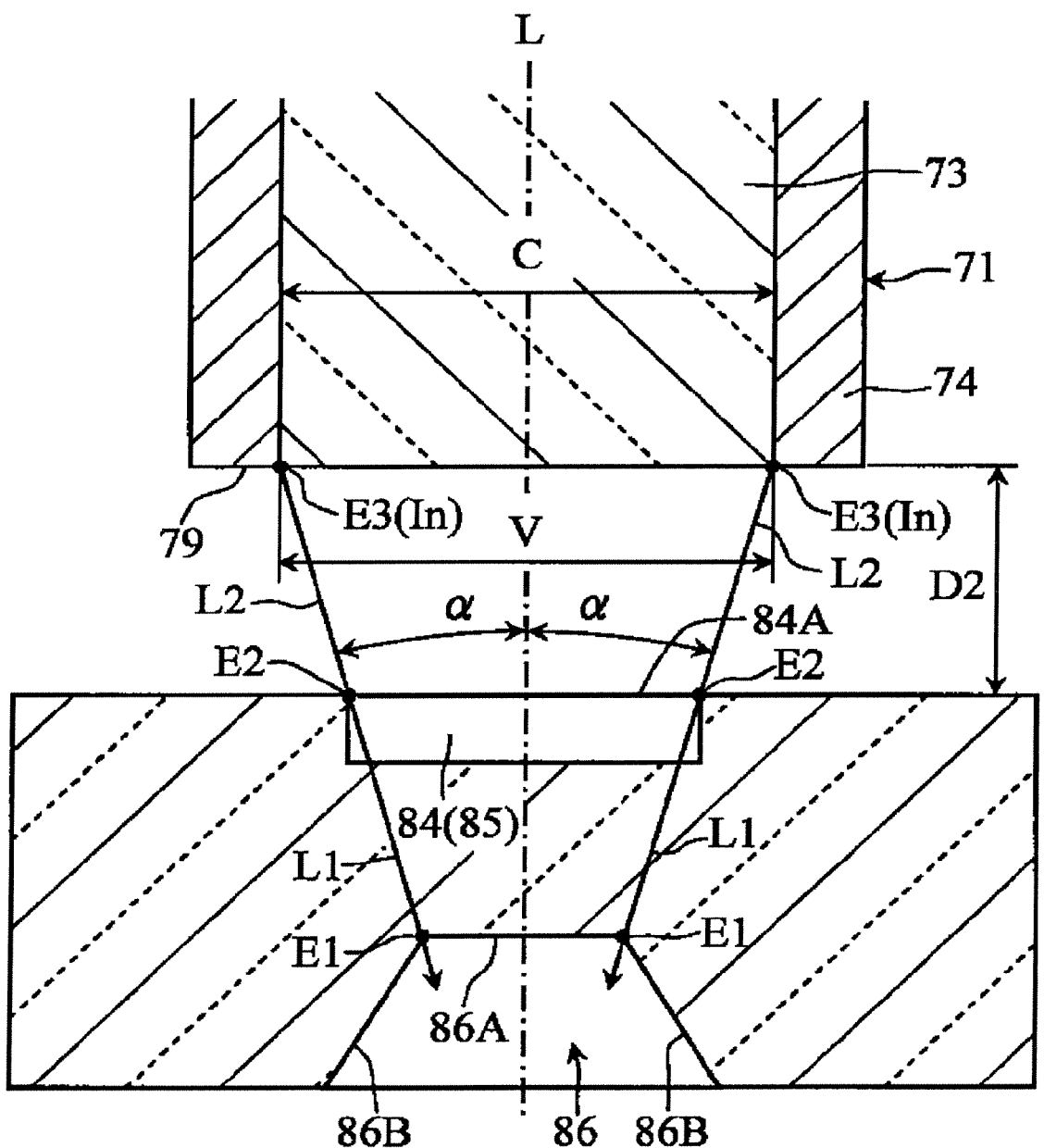
FIG. 20 is a cross-sectional view corresponding to FIG. 19 for explaining working and effect of the analyzing apparatus shown in FIG. 18.

FIG. 20 shows a case in which a relationship C=V is satisfied. It is presumed that the distance D between the light go-through end surface 79 in the optical fiber 71 and the top face 84A of the flow channel 84 (or the cell) is D2. In this case, the extension line L2 of the straight line L1 which interconnects the edge E1 of the light go-through surface 86A in the aperture 86 and the edge E2 of the top face 84A of the flow channel 84 (or the cell) intersects an interface In between the core 73 and the clad 74 in the light go-through end surface 79 of the optical fiber 71. That is, when the relationship C=V is satisfied, light which is emitted from the interface In of between the core 73 and the clad 74 and passes through the edge E2 of the flow channel 84 (or the cell) at the top-face-84A side passes through a boundary between the light go-through surface 86A of the aperture 86 and the light reflective surface 86B thereof.

Figure 21:
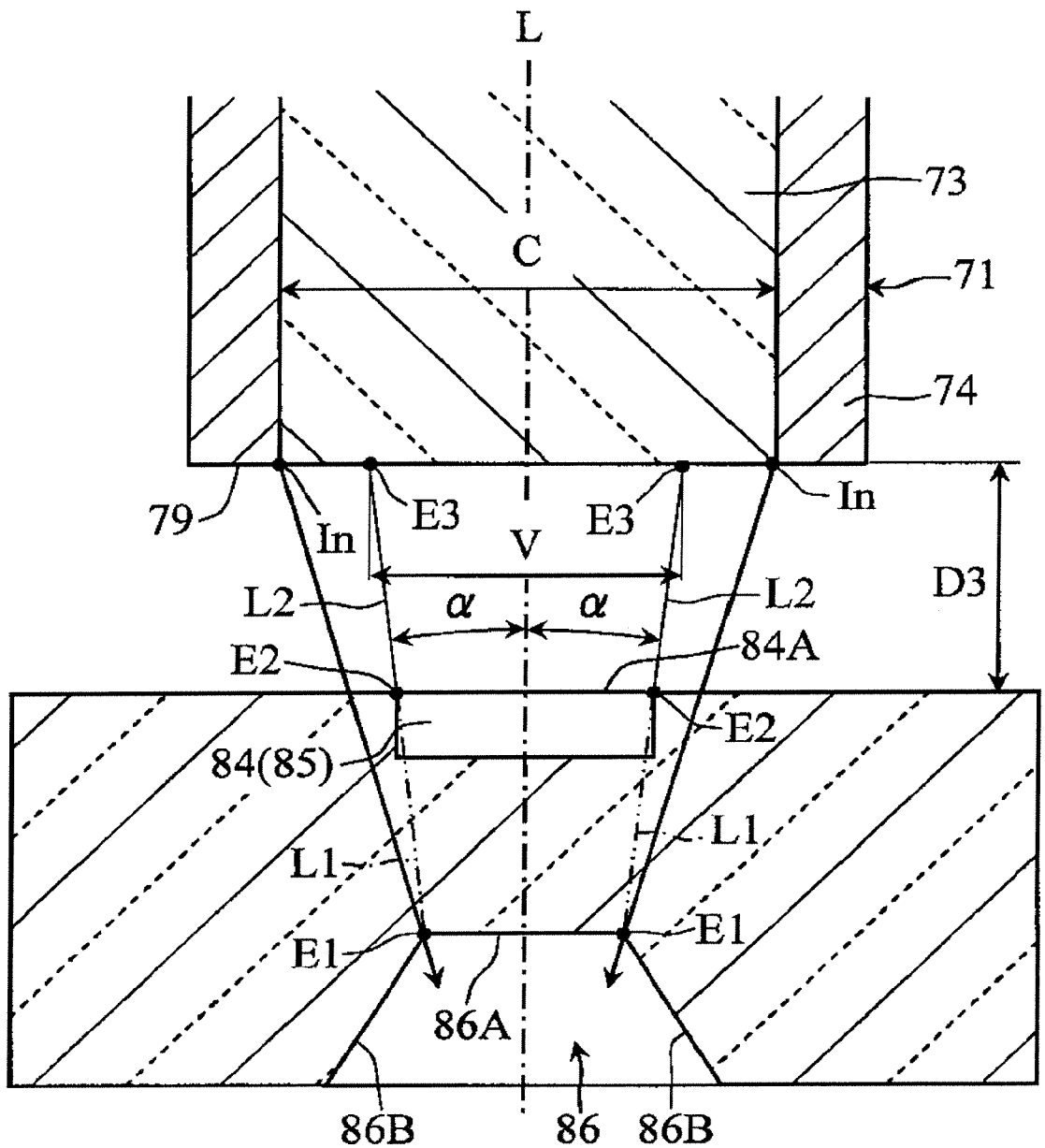
FIG. 21 is a cross-sectional view corresponding to FIG. 19 for explaining working and effect of the analyzing apparatus shown in FIG. 18.

FIG. 21 shows a case in which a relationship C>V is satisfied. The distance D between the light go-through end surface 79 in the optical fiber 71 and the top face 84A of the flow channel 84 (or the cell) is D3, and the distance D3 is shorter than the distance D2 which satisfies the relationship C=V. In this case, the extension line L2 of the straight line L1 which interconnects the edge E1 of the light go-through surface 86A of the aperture 86 and the edge E2 of the flow channel 84 (or the cell) at the top-face-84A side intersects the end surface 75 of the core 73 in the light go-through end surface 79 of the optical fiber 71. Therefore, when the relationship C>V is satisfied, light which is emitted from the interface In between the core 73 and the clad 74 and passes through the boundary between the light go-through surface 86A of the aperture 86 and the light reflective surface 86B thereof does not pass through the flow channel 84 (or the cell). Accordingly, when the relationship C>V (D3<D2) is satisfied, some of the light emitted from the end surface 75 of the core 73 passes through the light go-through surface of the aperture 86, and is received by the detecting unit 22 without passing through the flow channel 84 (or the cell).

In contrast, as shown in FIG. 19, when the relationship C<V is satisfied, the distance D3 between the light go-through end surface 79 of the optical fiber 71 and the top face 84A of the flow channel 84 (or the cell) becomes longer than the distance D2 in the case (C=V) shown in FIG. 20. Moreover, the extension line L2 of the straight line L1 which interconnects the edge E1 of the light go-through surface 86A of the aperture 86 and the edge E2 of the flow channel 84 (or the cell) at the top-face-84A side intersects the end surface of the core in the light go-through end surface 79 of the optical fiber 71 outwardly of the core 73. Therefore, when the relationship C<V is satisfied, light emitted from the interface between the core 73 and the clad 74 and passing through the boundary between the light go-through surface 86A of the aperture 86 and the light reflective surface 86B thereof passes through the flow channel 84 (or the cell). Accordingly, when the relationship C<V (D1>D2) is satisfied, light passing through the light go-through surface 86A is one which passes through the flow channel 84 (or the cell), and it becomes possible to prevent the light from passing through the light go-through surface of the aperture 86 without passing through the flow channel 84 (or the cell) and from being received by the detecting unit 22.

Therefore, by forming the bottom surface 87A of the concave portion 87 at a position where the relationship C<V (D1>D2) is satisfied, it is possible to prevent stray light which has not passed through the flow channel 84 (or the cell) from being received by the detecting unit 22 because such light does not pass through the light go-through surface 86A of the aperture 86. Accordingly, the analyzing apparatus 7 can improve the analytical precision.

According to the present invention, it is appropriate if the top face 84A of the flow channel 84 (or the cell) be formed at a position which satisfies the relationship C<V in the relationship with the optical fiber 71. That is, it is not necessary to arrange the optical fiber 71 so as to have the end surface 75 abutting the bottom face 87A of the concave portion 87, and the concave portion 87 is not always necessary.

Description of Reference Numerals

| | |
|---|---|
| 1, 1", 3, 4, 5, 6, 8 | Microchip |
| 10, 10", 84 | Flow channel |
| 11, 11", 32, 48, 54 | Substrate (Transparent member) |
| 14A, 14B, 31, 46, 47, 51, 81, 82 | Shading member |
| 15A" | Cell |
| 16, 16', 42, 43, 57, 60E, 61E, 86 | Aperture |
| 17, 17', 57A, 60Ea, 86A | Light go-through surface (of aperture) |
| 18, 18', 42A, 43A, 57B, 60Eb, 86B | Light reflective surface (of aperture) |
| 2, 2', 7 | Analyzing apparatus |
| 20 | Light source |
| 21 | Optical system |
| 30, 44, 45, 59 | Guide surface |
| 49, 58 | (V-shaped) Groove |
| 60 | Transparent member (Translucent member) |
| 61 | Transparent member (Second Translucent member) |
| 70 | Irradiating means |
| 71 | Optical fiber |
| 79 | Light go-through surface (of the optical fiber) |
| 83 | Cover |
| 87 | Concave portion (of the cover) |
| 88 | (Second) Concave portion (of the cover) |
| W1 | Width size (of the light go-through surface) |
| W2 | Width size (of the flow channel or the cell) |

The invention claimed is:

1. A microchip including:
a translucent member;
a flow channel or a cell formed at a side of the translucent member where light enters; and
an aperture formed in a position corresponding to the flow channel or the cell at a side of the translucent member where the light goes out, wherein
the aperture has a light go-through surface that causes light flux being emitted from the flow channel or the cell to go out, and a light reflective surface that totally reflects incident light flux,
a width size of the light go-through surface is smaller than a width size of the flow channel or the cell, and
the light flux that has been totally reflected by the light reflective surface does not travel toward the light go-through surface of the aperture.

2. The microchip according to claim 1, wherein
the light reflective surface includes a pair of inclined surfaces facing with each other, and
the pair of inclined surfaces is formed so that a distance between the pair of inclined surfaces becomes large as becoming apart from the light go-through surface.

3. The microchip according to claim 1, wherein
the light reflective surface includes a conical inclined surface, and
the conical inclined surface is formed so that a space of the conic becomes large as becoming apart from the light go-through surface.

4. The microchip according to claim 1 further includes a shading member preventing light from being emitted from portions other than the aperture.

5. The microchip according to claim 4, wherein the shading member is provided adjacent to the aperture.

6. The microchip according to claim 4, wherein the shading member is formed at a side face of the translucent member.

7. The microchip according to claim 4, wherein
the translucent member has a guide surface that guides light flux which does not passed through the light go-through surface to an exterior of the translucent member, and
the shading member absorbs the light flux guided by the guide surface to the exterior of the translucent member.

8. The microchip according to claim 7, wherein
a side face of the translucent member is made inclined, and the guide surface is the side face.

9. The microchip according to claim 7 further including a second flow channel or a cell formed at the side of the translucent member where light enters, and
a second aperture formed in a position corresponding to the second flow channel or the cell at the light go-through surface side of the translucent member,
wherein the guide surface is provided between the aperture and the second aperture.

10. The microchip according to claim 9 further including a groove with a V-shaped cross section formed at the side of the translucent member where light goes out, and
the guide surface is an inner surface of the groove.

11. The microchip according to claim 1 further including a cover that covers the flow channel or the cell at the side of the translucent member where light enters, and
the cover includes a concave portion for arranging an end of irradiating means that irradiates the flow channel or the cell with light.

12. The microchip according to claim 11, wherein
the irradiating means includes an optical fiber, and
the concave portion has a bottom face where a light go-through end surface of the optical fiber abuts or an end of the optical fiber including the light go-through end surface engages.

13. An analyzing apparatus using the microchip according to claim 11, the analyzing apparatus including irradiating means which irradiates the flow channel or the cell with light,
wherein the irradiating means is provided so that a light go-through end abuts or engages with a concave portion of the cover of the microchip.

14. The analyzing apparatus according to claim 13, wherein a second concave portion is formed at a bottom face of the concave portion.

15. The analyzing apparatus according to claim 13, wherein the irradiating means includes an optical fiber.

16. The microchip according to claim 1, wherein a bottom face of the flow channel or the cell and the light go-through surface of the aperture are arranged on a same or substantially same axis.

17. The microchip according to claim 16, wherein when the flow channel or the cell is irradiated with light by the irradiating means,
a light-entering surface through which light enters to the flow channel or the cell is formed at a position satisfying a relationship C<V, where
C is the size of the light go-through surface of the irradiating means
V is a distance of a portion where a straight line interconnecting the edge of a light irradiating surface of the flow channel or the cell and the edge of the light go-through surface of the aperture intersects with an end surface of the irradiating means.

18. The microchip according to claim 1 that is formed by pasting a second translucent member on the translucent member, wherein
the translucent member and the second translucent member have the aperture and a groove defining the flow channel, and the aperture and the groove are arranged at axisymmetric positions or at point-symmetrical positions in a planer view.

19. The microchip according to claim 18, wherein
the translucent member and the second translucent member each have a concave portion for positioning, and
the concave portions are arranged at axisymmetric positions or at point-symmetrical positions in a planer view.

20. An analyzing apparatus using the microchip according to claim 1, the analyzing apparatus including:
a light source; and
an optical system, wherein
the light source and the optical system are arranged so as to cause light flux to enter into the flow channel or the cell, and to go out from the aperture, and
the optical system can irradiate the flow channel or the cell with light flux spreading in a direction of a short axis of the light go-through surface of the aperture.

21. The analyzing apparatus according to claim 20, wherein the optical system can irradiate the flow channel or the cell with light flux having a long axis in the direction of the short axis of the light go-through surface of the aperture.

\* \* \* \* \*